(12) United States Patent
Noguchi et al.

(10) Patent No.: US 10,787,691 B2
(45) Date of Patent: Sep. 29, 2020

(54) METHOD FOR PRODUCING L-AMINO ACID

(71) Applicant: AJINOMOTO CO., INC., Tokyo (JP)

(72) Inventors: Hiromi Noguchi, Kanagawa (JP); Yo Nishiyama, Kanagawa (JP); Yoshihiro Ito, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/774,075

(22) Filed: Jan. 28, 2020

(65) Prior Publication Data
US 2020/0239920 A1 Jul. 30, 2020

(30) Foreign Application Priority Data

Jan. 28, 2019 (JP) ................................. 2019-012490

(51) Int. Cl.
| | | |
|---|---|---|
| C12N 15/09 | (2006.01) | |
| C07K 1/00 | (2006.01) | |
| C12P 7/02 | (2006.01) | |
| C12P 13/14 | (2006.01) | |
| C07K 14/265 | (2006.01) | |
| C12N 15/74 | (2006.01) | |

(52) U.S. Cl.
CPC ............ *C12P 13/14* (2013.01); *C07K 14/265* (2013.01); *C12N 15/74* (2013.01)

(58) Field of Classification Search
CPC ...... C12N 2511/00; C12N 15/09; C07K 1/00; C12P 7/02
See application file for complete search history.

(56) References Cited

U.S. PATENT DOCUMENTS

| | | | |
|---|---|---|---|
| 7,041,814 B1 * | 5/2006 | Weinstock | ........... C07K 14/265 435/252.3 |
| 2009/0246835 A1 | 10/2009 | Iwatani et al. | |
| 2009/0286290 A1 | 11/2009 | Hara et al. | |
| 2011/0212496 A1 | 9/2011 | Takikawa et al. | |
| 2016/0130618 A1 | 5/2016 | Hara et al. | |
| 2018/0044703 A1 | 2/2018 | Hara et al. | |
| 2019/0191708 A1 * | 6/2019 | Boyetchko | ............... C12N 1/20 |

FOREIGN PATENT DOCUMENTS

| | | |
|---|---|---|
| WO | WO2007/037503 A1 | 4/2007 |
| WO | WO2015/005406 A1 | 1/2015 |

OTHER PUBLICATIONS

Extended European Search Report for European Patent App. No. 20153775.0 (May 27, 2020).

* cited by examiner

*Primary Examiner* — Maryam Monshipouri
(74) *Attorney, Agent, or Firm* — Cermak Nakajima & McGowan LLP; Shelly Guest Cermak

(57) ABSTRACT

A method for producing an L-amino acid such as L-glutamic acid is provided. An L-amino acid is produced by culturing in a medium a bacterium having an L-amino acid-producing ability, which has been modified so that the activity of a c1795 protein is reduced or the activity of a protein of which the expression is repressed by a c1795 protein is increased, and collecting the L-amino acid from the medium or cells of the bacterium.

22 Claims, No Drawings
Specification includes a Sequence Listing.

SEQUENCE LISTING

```
<160> NUMBER OF SEQ ID NOS: 26

<210> SEQ ID NO 1
<211> LENGTH: 402
<212> TYPE: DNA
<213> ORGANISM: Pantoea ananatis

<400> SEQUENCE: 1
atgcttgatt atcgcttccc gacagctttg caaatggttc tgagcgtggc gatggcggag      60
caaatgggaa aacgctctac cagcgcgatt ctcgcttacg ggcttgaagc aaacccgagt     120
tttatccgca agttgatggt gccattaacg cgtgacggca ttattgtgtc tacgctggga     180
cgcaccggct ccattcatct tggccgaccg gcggcagaca tcaccctgcg tgatatttat     240
gtttccgtca ctgatgataa aaaacttggg ctgcgcgccc ggacgtcgcg ccgcgttgcc     300
tggtcagcgc caacctgtgc tggtatttta aatctatcgc agaagaagcc gagcaggcct     360
cacttgcggt cctggccaaa cgcacggtgg ccgatgcctt aa                        402

<210> SEQ ID NO 2
<211> LENGTH: 133
<212> TYPE: PRT
<213> ORGANISM: Pantoea ananatis

<400> SEQUENCE: 2

Met Leu Asp Tyr Arg Phe Pro Thr Ala Leu Gln Met Val Leu Ser Val
1               5                   10                  15

Ala Met Ala Glu Gln Met Gly Lys Arg Ser Thr Ser Ala Ile Leu Ala
            20                  25                  30

Tyr Gly Leu Glu Ala Asn Pro Ser Phe Ile Arg Lys Leu Met Val Pro
        35                  40                  45

Leu Thr Arg Asp Gly Ile Ile Val Ser Thr Leu Gly Arg Thr Gly Ser
    50                  55                  60

Ile His Leu Gly Arg Pro Ala Ala Asp Ile Thr Leu Arg Asp Ile Tyr
65                  70                  75                  80

Val Ser Val Thr Asp Asp Lys Lys Leu Gly Leu Arg Ala Arg Thr Ser
                85                  90                  95

Arg Arg Val Ala Trp Ser Ala Pro Thr Cys Ala Gly Ile Leu Asn Leu
            100                 105                 110

Ser Gln Lys Lys Pro Ser Arg Pro His Leu Arg Ser Trp Pro Asn Ala
        115                 120                 125

Arg Trp Pro Met Pro
    130

<210> SEQ ID NO 3
<211> LENGTH: 348
<212> TYPE: DNA
<213> ORGANISM: Pantoea ananatis
```

<400> SEQUENCE: 3

```
atgatgagta acgctttat tcacgacctg attagctgga tcgataacaa tatcgaagca    60
cgtctcgatc tcgacaccgt ttctgagcgc gctggctatt caaaatggca cctgcaacgg  120
atgtttaaag agcacaccgg ctatccactg ggtgaataca ttcgcatgaa gaagctgaaa  180
aaatcggccg accgtttgac cagcaccaac gagcctatcc tgaatgtagc gatatcgctg  240
ggatttgact cgcaacagtc ttttaaccgc agctttaagc gtcagtacgg tgttgccccg  300
ggtgcatggc gccgtcacac tgtgccttcg cagtcagcca tgcagtaa                348
```

<210> SEQ ID NO 4
<211> LENGTH: 115
<212> TYPE: PRT
<213> ORGANISM: Pantoea ananatis

<400> SEQUENCE: 4

```
Met Met Ser Asn Ala Phe Ile His Asp Leu Ile Ser Trp Ile Asp Asn
1               5                   10                  15

Asn Ile Glu Ala Arg Leu Asp Leu Asp Thr Val Ser Glu Arg Ala Gly
            20                  25                  30

Tyr Ser Lys Trp His Leu Gln Arg Met Phe Lys Glu His Thr Gly Tyr
        35                  40                  45

Pro Leu Gly Glu Tyr Ile Arg Met Lys Lys Leu Lys Lys Ser Ala Asp
    50                  55                  60

Arg Leu Thr Ser Thr Asn Glu Pro Ile Leu Asn Val Ala Ile Ser Leu
65                  70                  75                  80

Gly Phe Asp Ser Gln Gln Ser Phe Asn Arg Ser Phe Lys Arg Gln Tyr
                85                  90                  95

Gly Val Ala Pro Gly Ala Trp Arg Arg His Thr Val Pro Ser Gln Ser
            100                 105                 110

Ala Met Gln
        115
```

<210> SEQ ID NO 5
<211> LENGTH: 1155
<212> TYPE: DNA
<213> ORGANISM: Pantoea ananatis

<400> SEQUENCE: 5

```
atgattactc actgggttcg tcagggatct tccctgctgg gaatggggct gctggttagt    60
ctgctgagcg gttgtgacac gggccaggct aaaaatgccc cgccgccgcc gcccgacgtc  120
agcgttgcgg atgtattggt gaagcctgtc agtcaatggg acagcttcaa cgggcgcgtt  180
gaagccgtag aaagcgtgca gctccggcct cgcgtttcgg ttatatcga tagcgttaat  240
tatcatgaag gcgacgaggt caggaaaggt caggtcctgt ttaccatcga cgatcgcagc  300
taccgtgccg cactggaaca ggcaaaagcg acgctggccc gtgcgcgcag tcaggccagc  360
ctgacacgca gcgaatcggc acgcaccgag aagctggtgg gtacacaggc ggtgtcacgc  420
gagatgtggg aacagcgacg ttcgacagcc agtcaggctc aggctgatgt gcaggccgcc  480
gaatcctctg tcgacatggc tcaactcaat ctggatttta cccgcgtcac cgcgccgatt  540
gacggacggg ccagccgggc catgattact gccggtaatc ttgtcaccgc cggcgacagc  600
gccagcgtac ttaccacact ggtttcgcag gacaagatgt tcgtctattt cgacgtcgat  660
gagaccacct tcctgcacta tcaggctatg gcacgtcagg acaacagcg gcatgccctg  720
cccgttgaaa tcggcctggc tggcgaacag ggttatccac atcgcggcaa cgtcgatttt  780
```

-continued

```
cttgataacc aacttaatgc cagcaccggt acgatccgca tgcgcgccct tctggacaac    840
cgccagcgca cctatacgcc cggcctgttt gcccgcgttc gccttccggg tagcgcgcag    900
tttaatgccg tgttaatcga cgacaaagcc gtgctgaccg atcaggaccg caagtatgtc    960
tatgtggtcg atgcacaggg taaagcccaa cgtcgtgatg ttcatcccgg cgcgatggcg    1020
gacggattac gcatcgttac caccggttta caggcgggcg atcgggttat cgttgccggc    1080
ctgcaaaaag tgtttatgcc tggtatgccg gtaacggcaa aaaccgtcga tatggccgcg    1140
actgccgcgc gataa                                                     1155
```

<210> SEQ ID NO 6
<211> LENGTH: 384
<212> TYPE: PRT
<213> ORGANISM: Pantoea ananatis

<400> SEQUENCE: 6

```
Met Ile Thr His Trp Val Arg Gln Gly Ser Ser Leu Leu Gly Met Gly
1               5                   10                  15

Leu Leu Val Ser Leu Leu Ser Gly Cys Asp Thr Gly Gln Ala Lys Asn
            20                  25                  30

Ala Pro Pro Pro Pro Asp Val Ser Val Ala Asp Val Leu Val Lys
        35                  40                  45

Pro Val Ser Gln Trp Asp Ser Phe Asn Gly Arg Val Glu Ala Val Glu
    50                  55                  60

Ser Val Gln Leu Arg Pro Arg Val Ser Gly Tyr Ile Asp Ser Val Asn
65                  70                  75                  80

Tyr His Glu Gly Asp Glu Val Arg Lys Gly Gln Val Leu Phe Thr Ile
                85                  90                  95

Asp Asp Arg Ser Tyr Arg Ala Ala Leu Glu Gln Ala Lys Ala Thr Leu
            100                 105                 110

Ala Arg Ala Arg Ser Gln Ala Ser Leu Thr Arg Ser Glu Ser Ala Arg
        115                 120                 125

Thr Glu Lys Leu Val Gly Thr Gln Ala Val Ser Arg Glu Met Trp Glu
    130                 135                 140

Gln Arg Arg Ser Thr Ala Ser Gln Ala Gln Ala Asp Val Gln Ala Ala
145                 150                 155                 160

Glu Ser Ser Val Asp Met Ala Gln Leu Asn Leu Asp Phe Thr Arg Val
                165                 170                 175

Thr Ala Pro Ile Asp Gly Arg Ala Ser Arg Ala Met Ile Thr Ala Gly
            180                 185                 190

Asn Leu Val Thr Ala Gly Asp Ser Ala Ser Val Leu Thr Thr Leu Val
        195                 200                 205

Ser Gln Asp Lys Met Phe Val Tyr Phe Asp Val Asp Glu Thr Thr Phe
    210                 215                 220

Leu His Tyr Gln Ala Met Ala Arg Gln Gly Gln Gln Arg His Ala Leu
225                 230                 235                 240

Pro Val Glu Ile Gly Leu Ala Gly Glu Gln Gly Tyr Pro His Arg Gly
                245                 250                 255

Asn Val Asp Phe Leu Asp Asn Gln Leu Asn Ala Ser Thr Gly Thr Ile
            260                 265                 270

Arg Met Arg Ala Leu Leu Asp Asn Arg Gln Thr Tyr Thr Pro Gly
        275                 280                 285

Leu Phe Ala Arg Val Arg Leu Pro Gly Ser Ala Gln Phe Asn Ala Val
    290                 295                 300
```

```
Leu Ile Asp Asp Lys Ala Val Leu Thr Asp Gln Asp Arg Lys Tyr Val
305                 310                 315                 320

Tyr Val Val Asp Ala Gln Gly Lys Ala Gln Arg Arg Asp Val His Pro
                325                 330                 335

Gly Ala Met Ala Asp Gly Leu Arg Ile Val Thr Thr Gly Leu Gln Ala
                340                 345                 350

Gly Asp Arg Val Ile Val Ala Gly Leu Gln Lys Val Phe Met Pro Gly
                355                 360                 365

Met Pro Val Thr Ala Lys Thr Val Asp Met Ala Ala Thr Ala Ala Arg
        370                 375                 380

<210> SEQ ID NO 7
<211> LENGTH: 3156
<212> TYPE: DNA
<213> ORGANISM: Pantoea ananatis

<400> SEQUENCE: 7
```

| | | | | | |
|---|---|---|---|---|---|
| atggattttt | cccgcttttt | tattgatcgg | ccgatctttg | ccgccgtgct | gtccgtcttg | 60 |
| attttatga | ccgggctgat | cgccatcccg | ctgctgccca | tcagtgagta | tccggacgtg | 120 |
| gtgccgccca | gcgtgcaggt | gcgtgccgaa | tatcccggcg | ctaacccgaa | agccatcgcc | 180 |
| gactccgtgg | caacgccgct | ggaagaggcg | attaacggcg | ttgaaaacat | gatgtacatg | 240 |
| aagtccgtgg | ccggttctga | cggtgtgctg | gtgaccaccg | tgaccttccg | cccgggtacc | 300 |
| gatccggatc | aggcccaggt | tcaggtgcaa | aaccgcgtag | cccaggccga | ggcgcggttg | 360 |
| ccggaggacg | tgcgccgtct | cgggatcacg | acgcaaaaaa | tgtcgccgac | cctgacctta | 420 |
| gtggtgcatc | tgtttttccc | taataacacc | tacgattcgc | tctatctgcg | taactacgcc | 480 |
| acgctgaaag | tcaaagatga | gctggcccgt | ctgccgggcg | tggggcaaat | ccagatttt | 540 |
| ggcgcgggtg | aatacgcgat | gcgcgtctgg | ctcgatccca | caaagtggc | ggcgcgcggc | 600 |
| ttaaccgcct | cggacgttgt | gaaagcgatg | caggagcaga | acgtacaggt | ttctgcgggg | 660 |
| caacttgggg | cggaaccgtt | aaaaaaacag | agcgattttc | tgctgtccat | taatatgcaa | 720 |
| ggacggctgg | aaaacgagca | gcagtttggc | gatatcattc | tgaaaacgtc | agaggacggc | 780 |
| tcactggtcc | ggctgcgtga | cgtggcgcgc | attgaaatgg | gttcaggcag | ctatgccctg | 840 |
| cgttcgcagc | tcaataacaa | agacgccgtc | ggtattggta | ttttccaggc | accgggcgcc | 900 |
| aatgctatcg | atctgtcaaa | cgcggtcgt | gccaaaatgg | atgaactggc | cacccgtttc | 960 |
| ccgaacgatg | tgaagtgggc | tgcgccttac | gatcccaccg | tgtttgttcg | cgactccatt | 1020 |
| aaggctgtgg | tgcaaaccct | gctggaagcg | tgtttttag | tggtgctggt | ggtgattctg | 1080 |
| ttcctgcaaa | cctggcgcgc | ttccattatt | cccctgctgg | cggttccggt | atccgtagtc | 1140 |
| ggcaccttta | gcgtgctgta | tctgcttggg | ttctcgctca | acacgctaag | cctgttcgga | 1200 |
| ctggtgctgg | ccatcggtat | cgtggtggac | gatgccatcg | tggtggtgga | aaacgttgaa | 1260 |
| cgcaatattg | agatgggact | gtcacccaaa | gccgctgccc | atcaggcgat | gcgtgaggta | 1320 |
| tccggcccga | tcattgccat | cgccctcgtg | ctgtgtgcgg | tgttcgtgcc | catggcgttt | 1380 |
| ctgtcgggcg | tgaccggcca | gttttacaaa | cagttcgcca | ccacgattgc | gatttcaacc | 1440 |
| gtgatctccg | ctatcaactc | actgaccctg | tctcccgcac | tggccgcgat | gttactgaag | 1500 |
| gatcatcagg | cccccaaaga | tatgccgacg | cgcctgatcg | acaggctgtt | tggctggatt | 1560 |
| ttccgcccgt | taaccgcttc | tttcagcgt | agcgcgcacg | gctatgaatc | gatggtgggg | 1620 |
| aaaaccctgc | gtcgtcgcgg | cgcggtgttt | ggtgtttacc | tggtgttact | ggctggcgcg | 1680 |

```
ggctggatgt tcatgcggt gccaggtggg tttattccca ctcaggacaa gctttacctg    1740
atcggcggcg tcaaaatgcc ggaaggctcg tcgctggcgc gcaccgatga agtgattcgt    1800
cagatgagcg aaatcggcct gcaaacggaa ggcgtggcct atgcggtggc cttccccggc    1860
ctgaacgcgt tgcagtttac caatacgccg aacagcggca cggtcttttt tggcctgaag    1920
ccgttccgcg aacgtaaaca aacggcggcg cagataaacg cggagatcaa tgcgaaaatt    1980
tcccgcattc aacagggatt tggcttttca attatgccac cgcctatcct ggggctaggc    2040
cagggttcgg gctattccct ttacgttcag gatcgggccg gactgggcta tggcgcactg    2100
cagaccgcga ttaacaccct ctcgggcgcg gttatgcaga cgcccgggcat gcacttcccg    2160 atctcctctt atcaggccaa cgtgccacag ctggaggtgc aggtagaccg cgataaggcg    2220
aaagcacagg gctagcgtt aaccgatctg ttcagtacgc tacaaactta tctgggttca    2280
tcctacgtta atgactttaa ccgttttggg cgcacctggc gcgtgatggc gcaggccgac    2340
ggggaattcc gcgacagcgt tgaggacatc gcgaacctgc gtacccgtaa cgaccgcggt    2400
gagatggtgc cgattggcag catggtgcat atcaccacgg cctacggccc cgatccggtg    2460
attcgttata acggctatcc ggcggctgac ttgatcggcg atgccgatcc acgcgtgctc    2520
tcatcggccc aggcgatgcg tcaacttgaa acgatgtcgg tcagctgct gccgaacggc    2580 atgaatatcg aatggaccga tctcagctat cagcaggcga cgcagggtaa tacgcccctg    2640
attgttttcc ctgtcgctgt cctgttggcg ttttttagtg ctggctgcact gtatgagagc    2700 tggacgctgc cgcttgcggt gatcctgatt gtgccggtga ccatgctgtc tgcccttgtg    2760
ggcgtctggt taaccggtgg ggataacaac gtattcgtgc aggttggact ggtcgtgctg    2820
atggggctgg cctgtaagaa cgccattctg attgtggagt tcgcccgcga actggagatt    2880
cagggcaaag gcattacaga agcggcgctg gaagcctgcc gtctgcgcct gcgtcctatc    2940
gtaatgacct ctatcgcctt tattgccggc acgatccccc tgattctggg tgaaggtgcg    3000
ggtgctgaag tgcgtggcgt taccggcgtt accgtgttct ccggtatgtt aggcgttacg    3060
ctgtttggct tgttcctgac gccggtgttc tacgtgacgc tgcgcaagct ggtgacgcgt    3120
aaagccgctc tgcagcgctt acagaacgcg tcataa                              3156
```

<210> SEQ ID NO 8
<211> LENGTH: 1051
<212> TYPE: PRT
<213> ORGANISM: Pantoea ananatis

<400> SEQUENCE: 8

```
Met Asp Phe Ser Arg Phe Phe Ile Asp Arg Pro Ile Phe Ala Ala Val
1               5                   10                  15

Leu Ser Val Leu Ile Phe Met Thr Gly Leu Ile Ala Ile Pro Leu Leu
            20                  25                  30

Pro Ile Ser Glu Tyr Pro Asp Val Pro Pro Ser Val Gln Val Arg
        35                  40                  45

Ala Glu Tyr Pro Gly Ala Asn Pro Lys Ala Ile Ala Asp Ser Val Ala
    50                  55                  60

Thr Pro Leu Glu Glu Ala Ile Asn Gly Val Glu Asn Met Met Tyr Met
65                  70                  75                  80

Lys Ser Val Ala Gly Ser Asp Gly Val Leu Val Thr Thr Val Thr Phe
                85                  90                  95

Arg Pro Gly Thr Asp Pro Asp Gln Ala Gln Val Gln Val Gln Asn Arg
            100                 105                 110
```

-continued

Val Ala Gln Ala Glu Ala Arg Leu Pro Glu Asp Val Arg Leu Gly
115                 120                 125

Ile Thr Thr Gln Lys Met Ser Pro Thr Leu Thr Leu Val Val His Leu
130                 135                 140

Phe Ser Pro Asn Asn Thr Tyr Asp Ser Leu Tyr Leu Arg Asn Tyr Ala
145                 150                 155                 160

Thr Leu Lys Val Lys Asp Glu Leu Ala Arg Leu Pro Gly Val Gly Gln
                165                 170                 175

Ile Gln Ile Phe Gly Ala Gly Glu Tyr Ala Met Arg Val Trp Leu Asp
                180                 185                 190

Pro Asn Lys Val Ala Ala Arg Gly Leu Thr Ala Ser Asp Val Val Lys
                195                 200                 205

Ala Met Gln Glu Gln Asn Val Gln Val Ser Ala Gly Gln Leu Gly Ala
210                 215                 220

Glu Pro Leu Lys Lys Gln Ser Asp Phe Leu Leu Ser Ile Asn Met Gln
225                 230                 235                 240

Gly Arg Leu Glu Asn Glu Gln Gln Phe Gly Asp Ile Ile Leu Lys Thr
                245                 250                 255

Ser Glu Asp Gly Ser Leu Val Arg Leu Arg Asp Val Ala Arg Ile Glu
                260                 265                 270

Met Gly Ser Gly Ser Tyr Ala Leu Arg Ser Gln Leu Asn Asn Lys Asp
                275                 280                 285

Ala Val Gly Ile Gly Ile Phe Gln Ala Pro Gly Ala Asn Ala Ile Asp
                290                 295                 300

Leu Ser Asn Ala Val Arg Ala Lys Met Asp Glu Leu Ala Thr Arg Phe
305                 310                 315                 320

Pro Asn Asp Val Lys Trp Ala Ala Pro Tyr Asp Pro Thr Val Phe Val
                325                 330                 335

Arg Asp Ser Ile Lys Ala Val Val Gln Thr Leu Leu Glu Ala Val Phe
                340                 345                 350

Leu Val Val Leu Val Val Ile Leu Phe Leu Gln Thr Trp Arg Ala Ser
                355                 360                 365

Ile Ile Pro Leu Leu Ala Val Pro Val Ser Val Gly Thr Phe Ser
370                 375                 380

Val Leu Tyr Leu Leu Gly Phe Ser Leu Asn Thr Leu Ser Leu Phe Gly
385                 390                 395                 400

Leu Val Leu Ala Ile Gly Ile Val Val Asp Asp Ala Ile Val Val Val
                405                 410                 415

Glu Asn Val Glu Arg Asn Ile Glu Met Gly Leu Ser Pro Lys Ala Ala
                420                 425                 430

Ala His Gln Ala Met Arg Glu Val Ser Gly Pro Ile Ile Ala Ile Ala
                435                 440                 445

Leu Val Leu Cys Ala Val Phe Val Pro Met Ala Phe Leu Ser Gly Val
450                 455                 460

Thr Gly Gln Phe Tyr Lys Gln Phe Ala Thr Thr Ile Ala Ile Ser Thr
465                 470                 475                 480

Val Ile Ser Ala Ile Asn Ser Leu Thr Leu Ser Pro Ala Leu Ala Ala
                485                 490                 495

Met Leu Leu Lys Asp His Gln Ala Pro Lys Asp Met Pro Thr Arg Leu
                500                 505                 510

Ile Asp Arg Leu Phe Gly Trp Ile Phe Arg Pro Phe Asn Arg Phe Phe
                515                 520                 525

-continued

```
Gln Arg Ser Ala His Gly Tyr Glu Ser Met Val Gly Lys Thr Leu Arg
        530                 535                 540

Arg Arg Gly Ala Val Phe Gly Val Tyr Leu Val Leu Leu Ala Gly Ala
545                 550                 555                 560

Gly Trp Met Phe His Ala Val Pro Gly Gly Phe Ile Pro Thr Gln Asp
                565                 570                 575

Lys Leu Tyr Leu Ile Gly Gly Val Lys Met Pro Glu Gly Ser Ser Leu
                580                 585                 590

Ala Arg Thr Asp Glu Val Ile Arg Gln Met Ser Glu Ile Gly Leu Gln
            595                 600                 605

Thr Glu Gly Val Ala Tyr Ala Val Ala Phe Pro Gly Leu Asn Ala Leu
        610                 615                 620

Gln Phe Thr Asn Thr Pro Asn Ser Gly Thr Val Phe Phe Gly Leu Lys
625                 630                 635                 640

Pro Phe Arg Glu Arg Lys Gln Thr Ala Ala Gln Ile Asn Ala Glu Ile
                645                 650                 655

Asn Ala Lys Ile Ser Arg Ile Gln Gln Gly Phe Gly Phe Ser Ile Met
                660                 665                 670

Pro Pro Pro Ile Leu Gly Leu Gly Gln Gly Ser Gly Tyr Ser Leu Tyr
            675                 680                 685

Val Gln Asp Arg Ala Gly Leu Gly Tyr Gly Ala Leu Gln Thr Ala Ile
        690                 695                 700

Asn Thr Leu Ser Gly Ala Val Met Gln Thr Pro Gly Met His Phe Pro
705                 710                 715                 720

Ile Ser Ser Tyr Gln Ala Asn Val Pro Gln Leu Glu Val Gln Val Asp
                725                 730                 735

Arg Asp Lys Ala Lys Ala Gln Gly Val Ala Leu Thr Asp Leu Phe Ser
                740                 745                 750

Thr Leu Gln Thr Tyr Leu Gly Ser Ser Tyr Val Asn Asp Phe Asn Arg
            755                 760                 765

Phe Gly Arg Thr Trp Arg Val Met Ala Gln Ala Asp Gly Glu Phe Arg
        770                 775                 780

Asp Ser Val Glu Asp Ile Ala Asn Leu Arg Thr Arg Asn Asp Arg Gly
785                 790                 795                 800

Glu Met Val Pro Ile Gly Ser Met Val His Ile Thr Thr Ala Tyr Gly
                805                 810                 815

Pro Asp Pro Val Ile Arg Tyr Asn Gly Tyr Pro Ala Ala Asp Leu Ile
                820                 825                 830

Gly Asp Ala Asp Pro Arg Val Leu Ser Ser Ala Gln Ala Met Arg Gln
            835                 840                 845

Leu Glu Thr Met Ser Gly Gln Leu Leu Pro Asn Gly Met Asn Ile Glu
        850                 855                 860

Trp Thr Asp Leu Ser Tyr Gln Gln Ala Thr Gln Gly Asn Thr Ala Leu
865                 870                 875                 880

Ile Val Phe Pro Val Ala Val Leu Leu Ala Phe Leu Val Leu Ala Ala
                885                 890                 895

Leu Tyr Glu Ser Trp Thr Leu Pro Leu Ala Val Ile Leu Ile Val Pro
            900                 905                 910

Val Thr Met Leu Ser Ala Leu Val Gly Val Trp Leu Thr Gly Gly Asp
        915                 920                 925

Asn Asn Val Phe Val Gln Val Gly Leu Val Val Leu Met Gly Leu Ala
930                 935                 940
```

-continued

```
Cys Lys Asn Ala Ile Leu Ile Val Glu Phe Ala Arg Glu Leu Glu Ile
945                 950                 955                 960

Gln Gly Lys Gly Ile Thr Glu Ala Ala Leu Glu Ala Cys Arg Leu Arg
            965                 970                 975

Leu Arg Pro Ile Val Met Thr Ser Ile Ala Phe Ile Ala Gly Thr Ile
        980                 985                 990

Pro Leu Ile Leu Gly Glu Gly Ala  Gly Ala Glu Val Arg  Gly Val Thr
    995                 1000                 1005

Gly Val  Thr Val Phe Ser Gly  Met Leu Gly Val Thr  Leu Phe Gly
    1010                 1015                 1020

Leu Phe  Leu Thr Pro Val Phe  Tyr Val Thr Leu Arg  Lys Leu Val
    1025                 1030                 1035

Thr Arg  Lys Ala Ala Leu Gln  Arg Leu Gln Asn Ala  Ser
    1040                 1045                 1050
```

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
ccatgattac gaattatgct tgattatcgc ttccc    35

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttaaggcatc ggccaccgtg    20

<210> SEQ ID NO 11
<211> LENGTH: 45
<212> TYPE: DNA
<213> ORGANISM: Artificial Sequence
<220> FEATURE:
<223> OTHER INFORMATION: primer

<400> SEQUENCE: 11
tggccgatgc cttaatgaag cctgctttt tatactaagt tggca    45

<210> SEQ ID NO 12
<211> LENGTH: 45
<212> TYPE: DNA
<213> ORGANISM: Artificial Sequence
<220> FEATURE:
<223> OTHER INFORMATION: primer

<400> SEQUENCE: 12
atgcctgcag gtcgacgctc aagttagtat aaaaaagctg aacga    45

<210> SEQ ID NO 13
<211> LENGTH: 30
<212> TYPE: DNA
<213> ORGANISM: Artificial Sequence
<220> FEATURE:
<223> OTHER INFORMATION: primer

```
<400> SEQUENCE: 13
ctgatgataa aaaactctag gctgcgcgcc                                    30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
tgacggaaac ataaatatca cgcagggtga                                    30

<210> SEQ ID NO 15
<211> LENGTH: 80
<212> TYPE: DNA
<213> ORGANISM: Artificial Sequence
<220> FEATURE:
<223> OTHER INFORMATION: primer

<400> SEQUENCE: 15
ctcatgcggc aatacaacaa caaaaacgca ccgcaattca ggatacaaag atgcttgatt   60
atcgcttccc gacagctttg                                               80

<210> SEQ ID NO 16
<211> LENGTH: 80
<212> TYPE: DNA
<213> ORGANISM: Artificial Sequence
<220> FEATURE:
<223> OTHER INFORMATION: primer

<400> SEQUENCE: 16
cggttccggt acggcggtgc agttgctggt atcgtgggtt ttcagctcat cgctcaagtt   60
agtataaaaa agctgaacga                                               80

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
acgcgtcgac atgatgagta acgcttttat tcac                               34

<210> SEQ ID NO 18
<211> LENGTH: 34
<212> TYPE: DNA
<213> ORGANISM: Artificial Sequence
<220> FEATURE:
<223> OTHER INFORMATION: primer

<400> SEQUENCE: 18
ctagtctaga ttactgcatg gctgactgcg aagg                               34

<210> SEQ ID NO 19
<211> LENGTH: 6883
<212> TYPE: DNA
<213> ORGANISM: Artificial Sequence
<220> FEATURE:
<223> OTHER INFORMATION: plasmid
```

<400> SEQUENCE: 19

```
gggggtaaat ggcactacag gcgccttttt tggattcatg caaggaaact acccataata    60
caagaaaagc ccgtcacggg cttctcaggg cgttttatgg cgggtctgct atgtggtgct   120
atctgacttt ttgctgttca gcagttcctg ccctctgatt ttccagtctg accacttcgg   180
attatcccgt gacaggtcat tcagactggc taatgcaccc agtaaggcag cggtatcatc   240
aacaggctta cccgtcttac tgtcaattct tgaagacgaa agggcctcgt gatacgccta   300
tttttatagg ttaatgtcat gataataatg gtttcttaga cgtcaggtgg cacttttcgg   360
ggaaatgtgc gcggaacccc tatttgttta ttttttctaaa tacattcaaa tatgtatccg   420
ctcatgagac aataaccctg ataaatgctt caataatatt gaaaaggaa gagtatgagt   480
attcaacatt tccgtgtcgc ccttattccc ttttttgcgg catttgcct tcctgttttt   540
gctcacccag aaacgctggt gaaagtaaaa gatgctgaag atcagttggg tgcacgagtg   600
ggttacatcg aactggatct caacagcggt aagatccttg agagttttcg ccccgaagaa   660
cgttttccaa tgatgagcac ttttaaagtt ctgctatgtg gcgcggtatt atcccgtgtt   720
gacgccgggc aagagcaact cggtcgccgc atacactatt ctcagaatga cttggttgag   780
tactcaccag tcacagaaaa gcatcttacg gatggcatga cagtaagaga attatgcagt   840
gctgccataa ccatgagtga taacactgcg gccaacttac ttctgacaac gatcggagga   900
ccgaaggagc taaccgcttt tttgcacaac atggggatc atgtaactcg ccttgatcgt   960
tgggaaccgg agctgaatga agccatacca aacgacgagc gtgacaccac gatgcctgca  1020
gcaatggcaa caacgttgcg caaactatta actggcgaac tacttactct agcttccgg  1080
caacaattaa tagactggat ggaggcggat aaagttgcag gaccacttct gcgctcggcc  1140
cttccggctg gctggtttat tgctgataaa tctggagccg gtgagcgtgg gtctcgcggt  1200
atcattgcag cactggggcc agatggtaag ccctcccgta tcgtagttat ctacacgacg  1260
gggagtcagg caactatgga tgaacgaaat agacagatcg ctgagatagg tgcctcactg  1320
attaagcatt ggtaactgtc agaccaagtt tactcatata ctttagat tgatttaaaa  1380
cttcattttt aatttaaaag gatctaggtg aagatccttt tgataatct catgaccaaa  1440
atcccttaac gtgagttttc gttccactga gcgtcagacc ccgtagaaaa gatcaaagga  1500
tcttcttgag atcctttttt tctgcgcgta atctgctgct tgcaaacaaa aaaaccaccg  1560
ctaccagcgg tggtttgttt gccggatcaa gagctaccaa ctctttttcc gaaggtaact  1620
ggcttcagca gagcgcagat accaaatact gtccttctag tgtagccgta gttaggccac  1680
cacttcaaga actctgtagc accgcctaca tacctcgctc tgctaatcct gttaccagtg  1740
gctgctgcca gtggcgataa gtcgtgtctt accgggttgg actcaagacg atagttaccg  1800
gataaggcgc agcggtcggg ctgaacgggg ggttcgtgca cacagcccag cttggagcga  1860
acgacctaca ccgaactgag atacctacag cgtgagcatt gagaaagcgc ccaatacgca  1920
aaccgcctct ccccgcgcgt tggccgattc attaatgcag ctggcgtaat agcgaagagg  1980
cccgcaccga tcgcccttcc caacagttgc gcagcctgaa tggcgaatgg cgctatttct  2040
tccagaattg ccatgatttt ttccccacgg gaggcgtcac tggctcccgt gttgtcggca  2100
gctttgattc gataagcagc atcgcctgtt tcaggctgtc tatgtgtgac tgttgagctg  2160
taacaagttg tctcaggtgt tcaatttcat gttctagttg ctttgttta ctggtttcac  2220
ctgttctatt aggtgttaca tgctgttcat ctgttacatt gtcgatcgt tcatggtgaa  2280
cagctttgaa tgcaccaaaa actcgtaaaa gctctgatgt atctatcttt tttacaccgt  2340
```

```
tttcatctgt gcatatggac agttttccct tgatatgta acggtgaaca gttgttctac    2400
ttttgtttgt tagtcttgat gcttcactga tagatacaag agccataaga acctcagatc    2460
cttccgtatt tagccagtat gttctctagt gtggttcgtt gttttttgcgt gagccatgag    2520 aacgaaccat tgagatcatg cttactttgc atgtcactca aaaattttgc ctcaaaactg    2580
gtgagctgaa ttttttgcagt taaagcatcg tgtagtgttt ttcttagtcc gttacgtagg    2640
taggaatctg atgtaatggt tgttggtatt ttgtcaccat tcatttttat ctggttgttc    2700
tcaagttcgg ttacgagatc catttgtcta tctagttcaa cttggaaaat caacgtatca    2760
gtcgggcggc ctcgcttatc aaccaccaat ttcatattgc tgtaagtgtt taaatcttta    2820
cttattggtt tcaaaaccca ttggttaagc cttttaaact catggtagtt attttcaagc    2880
attaacatga acttaaattc atcaaggcta atctctatat ttgccttgtg agttttcttt    2940
tgtgttagtt cttttaataa ccactcataa atcctcatag agtatttgtt ttcaaaagac    3000
ttaacatgtt ccagattata ttttatgaat ttttttaact ggaaaagata aggcaatatc    3060
tcttcactaa aaactaattc taattttttcg cttgagaact tggcatagtt tgtccactgg    3120
aaaatctcaa agcctttaac caaaggattc ctgatttcca cagttctcgt catcagctct    3180
ctggttgctt tagctaatac accataagca ttttccctac tgatgttcat catctgagcg    3240
tattggttat aagtgaacga taccgtccgt tctttccttg tagggttttc aatcgtgggg    3300
ttgagtagtg ccacacagca taaaattagc ttggtttcat gctccgttaa gtcatagcga    3360
ctaatcgcta gttcatttgc tttgaaaaca actaattcag acatacatct caattggtct    3420
taggtgatta atcactatac caatggagat gggctagtca atgatattac tagtcctttt    3480 cctttttgagt tgtgggtatc tgtaaattct gctagacctt tgctggaaaa cttgtaaatt    3540
ctgctagacc ctctgtaaat tccgctagac cttttgtgtgt ttttttttgtt tatattcaag    3600 tggttataat ttatagaata aagaaagaat aaaaaaagat aaaaagaata gatcccagcc    3660
ctgtgtataa ctcactactt tagtcagttc cgcagtatta caaaaggatg tcgcaaacgc    3720
tgtttgctcc tctacaaaac agaccttaaa accctaaagg cttaagtagc accctcgcaa    3780
gctcgggcaa atcgctgaat attccttttg tctccgacca tcaggcacct gagtcgctgt    3840 cttttttcgtg acattcagtt cgctgcgctc acggctctgg cagtgaatgg gggttgtatt    3900
gattcacttg aagtacgaaa aaaaccggga ggacattgga ttattcggga tctgatggga    3960
ttagatttgg tggggcttgc aagcctgtag tgcaaatttt agtcgttaat caatgaaacg    4020
cgaaagatag taaaaaattg cttttgtttc attgaaaata cgaaaaacaa aaacactgca    4080
aatcatttca ataacagctt caaaaaacgt tcaaaaccga taacaaccaa gctgtcacca    4140
aatgactcat atcacaaatc agcttatgcc gtttaggtat gttacatgtg tgattatgtg    4200
aggtgaagta tgttttagct ggttcatggt tgttatacgg cttttttttac ctcctgtggt    4260 tcctgtgaag gtactacaac actttcctgt tcatgaatcc catactttga caaaatctct    4320
ttgcgttttt cttcaggtaa tgcagtggtc gaaaaaaaaa gcccgcactg tcaggtgcgg    4380
gcttttttct gtgttaagct tgcatgcatt ccaactgcgc taatgacgca gctggacgaa    4440
ggcgggattc tcgtcttacc cgtaggggag gagcaccagt atttgaaacg ggtgcgtcgt    4500
cggggaggcg aatttattat cgataccgtg gaggccgtgc gctttgtccc tttagtgaag    4560
ggtgagctgg cttaaaacgt gaggaaatac ctggattttt cctggttatt tgccgcagg    4620 tcagcgtata atgaagatct tttccagtgt tgacaagggt gccttgcacg gttataatgt    4680
cactggttat taaccaattt ttcctggggg tcgacatgat gagtaacgct tttattcacg    4740
```

```
acctgattag ctggatcgat aacaatatcg aagcacgtct cgatctcgac accgtttctg    4800
agcgcgctgg ctattcaaaa tggcacctgc aacggatgtt taaagagcac accggctatc    4860
cactgggtga atacattcgc atgaagaagc tgaaaaaatc ggccgaccgt ttgaccagca    4920
ccaacgagcc tatcctgaat gtagcgatat cgctgggatt tgactcgcaa cagtctttta    4980
accgcagctt taagcgtcag tacggtgttg ccccgggtgc atggcgccgt cacactgtgc    5040
cttcgcagtc agccatgcag taatctagaa aacagaattt gcctggcggc agtagcgcgg    5100
tggtcccacc tgaccccatg ccgaactcag aagtgaaacg ccgtagcgcc gatggtagtg    5160
tggggtctcc ccatgcgaga gtagggaact gccaggcatc aaataaaacg aaaggctcag    5220
tcgaaagact gggcctttcg ttttatctgt tgtttgtcgg tgaacgctct cctgagtagg    5280
acaaatccgc cgggagcgga tttgaacgtt gcgaagcaac ggcccggagg gtggcgggca    5340
ggacgcccgc cataaactgc caggcatcaa attaagcaga aggccatcct gacggatggc    5400 cttttttgcgt ttctacaaac tcttcctggg atcctgcatt cgcgaggtac cgagctccgc    5460
tcaagttagt ataaaaagc tgaacggtaa acgtaaaatg atataaatat caatatatta    5520
aattagattt tgcataaaaa acagactaca taatactgta aaacacaaca tatgcagtca    5580
ctatgaatca actacttaga tggtattagt gacctgtaac agactgcagc tgatgtccgg    5640
cggtgctttt gccgttacgc accacccgt cagtagctga acaggaggga cagctgatag    5700
aaacagaagc cactggagca cctcaaaaac accatcatac actaaatcag taagttggca    5760
gcatcacccg acgcactttg cgccgaataa atacctgtga cggaagatca cttcgcagaa    5820
taaataaatc ctggtgtccc tgttgatacc gggaagccct gggccaactt ttggcgaaaa    5880
tgagacgttg atcggcacgt aagaggttcc aactttcacc ataatgaaat aagatcacta    5940
ccgggcgtat ttttgagtt atcgagattt tcaggagcta aggaagctaa aatgagaaa    6000 aaaatcactg gatataccac cgttgatata tcccaatggc atcgtaaaga acattttgag    6060
gcatttcagt cagttgctca atgtacctat aaccagaccg ttcagctgga tattacggcc    6120
tttttaaaga ccgtaaagaa aaataagcac aagttttatc cggcctttat tcacattctt    6180
gcccgcctga tgaatgctca tccggaattc cgtatggcaa tgaaagacgg tgagctggtg    6240
atatgggata gtgttcaccc ttgttacacc gttttccatg agcaaactga aacgttttca    6300
tcgctctgga gtgaatacca cgacgatttc cggcagtttc tacacatata ttcgcaagat    6360
gtggcgtgtt acggtgaaaa cctggcctat ttccctaaag ggtttattga gaatatgttt    6420
ttcgtctcag ccaatccctg ggtgagtttc accagttttg atttaaacgt ggccaatatg    6480
gacaacttct tcgcccccgt tttcaccatg ggcaaatatt atacgcaagg cgacaaggtg    6540
ctgatgccgc tggcgattca ggttcatcat gccgtctgtg atggcttcca tgtcggcaga    6600
atgcttaatg aattacaaca gtactgcgat gagtggcagg cggggcgta actcgacgaa    6660 atcaaataat gatttattt ggactgatag tgacctgttc gttgcaacaa attgataagc    6720
aatgcttttt tataatgcca acttagtata aaaaagcagg cttcaagatc cccatgtaat    6780
gaataaaaag cagtaattaa tacatctgtt tcatttgaag cgcgaaagct aaagttttcg    6840
catttatcgt gaaacgcttt cgcgtttttc gtgcgccgct tca    6883
```

<210> SEQ ID NO 20
<211> LENGTH: 34
<212> TYPE: DNA
<213> ORGANISM: Artificial Sequence
<220> FEATURE:
<223> OTHER INFORMATION: primer

```
<400> SEQUENCE: 20
accgctcgag atgattactc actgggttcg tcag                                34

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
ctagtctaga ttatgacgcg ttctgtaagc gctg                                34

<210> SEQ ID NO 22
<211> LENGTH: 10858
<212> TYPE: DNA
<213> ORGANISM: Artificial Sequence
<220> FEATURE:
<223> OTHER INFORMATION: plasmid

<400> SEQUENCE: 22
gggggtaaat ggcactacag gcgccttta tggattcatg caaggaaact acccataata      60
caagaaaagc ccgtcacggg cttctcaggg cgttttatgg cgggtctgct atgtggtgct    120
atctgacttt ttgctgttca gcagttcctg ccctctgatt ttccagtctg accacttcgg    180
attatcccgt gacaggtcat tcagactggc taatgcaccc agtaaggcag cggtatcatc    240
aacaggctta cccgtcttac tgtcaattct tgaagacgaa agggcctcgt gatacgccta    300
tttttatagg ttaatgtcat gataataatg gtttcttaga cgtcaggtgg cacttttcgg    360
ggaaatgtgc gcggaacccc tatttgttta ttttctaaa tacattcaaa tatgtatccg    420
ctcatgagac aataaccctg ataaatgctt caataatatt gaaaaggaa gagtatgagt    480 attcaacatt tccgtgtcgc ccttattccc ttttttgcgg cattttgcct tcctgttttt    540
gctcacccag aaacgctggt gaaagtaaaa gatgctgaag atcagttggg tgcacgagtg    600
ggttacatcg aactggatct caacagcggt aagatccttg agagttttcg ccccgaagaa    660
cgttttccaa tgatgagcac ttttaaagtt ctgctatgtg gcgcggtatt atcccgtgtt    720
gacgccgggc aagagcaact cggtcgccgc atacactatt ctcagaatga cttggttgag    780
tactcaccag tcacagaaaa gcatcttacg gatggcatga cagtaagaga attatgcagt    840
gctgccataa ccatgagtga taacactgcg gccaacttac ttctgacaac gatcggagga    900
ccgaaggagc taaccgcttt tttgcacaac atggggatc atgtaactcg ccttgatcgt    960
tgggaaccgg agctgaatga agccatacca aacgacgagc gtgacaccac gatgcctgca   1020
gcaatggcaa caacgttgcg caaactatta actggcgaac tacttactct agcttcccgg   1080
caacaattaa tagactggat ggaggcggat aaagttgcag gaccacttct gcgctcggcc   1140
cttccggctg gctggtttat tgctgataaa tctggagccg gtgagcgtgg gtctcgcggt   1200
atcattgcag cactggggcc agatggtaag ccctcccgta tcgtagttat ctacacgacg   1260
gggagtcagg caactatgga tgaacgaaat agacagatcg ctgagatagg tgcctcactg   1320
attaagcatt ggtaactgtc agaccaagtt tactcatata tactttagat tgatttaaaa   1380 cttcatttt aatttaaaag gatctaggtg aagatccttt ttgataatct catgaccaaa   1440
atcccttaac gtgagttttc gttccactga gcgtcagacc ccgtagaaaa gatcaaagga   1500
tcttcttgag atccttttt tctgcgcgta atctgctgct tgcaaacaaa aaaaccaccg   1560
ctaccagcgg tggtttgttt gccggatcaa gagctaccaa ctctttttcc gaaggtaact   1620
```

```
ggcttcagca gagcgcagat accaaatact gtccttctag tgtagccgta gttaggccac    1680
cacttcaaga actctgtagc accgcctaca tacctcgctc tgctaatcct gttaccagtg    1740
gctgctgcca gtggcgataa gtcgtgtctt accgggttgg actcaagacg atagttaccg    1800
gataaggcgc agcggtcggg ctgaacgggg ggttcgtgca cacagcccag cttggagcga    1860
acgacctaca ccgaactgag atacctacag cgtgagcatt gagaaagcgc ccaatacgca    1920
aaccgcctct ccccgcgcgt tggccgattc attaatgcag ctggcgtaat agcgaagagg    1980
cccgcaccga tcgcccttcc caacagttgc gcagcctgaa tggcgaatgg cgctatttct    2040
tccagaattg ccatgatttt tccccacgtg gaggcgtcac tggctcccgt gttgtcggca    2100
gctttgattc gataagcagc atcgcctgtt tcaggctgtc tatgtgtgac tgttgagctg    2160
taacaagttg tctcaggtgt tcaatttcat gttctagttg ctttgtttta ctggtttcac    2220
ctgttctatt aggtgttaca tgctgttcat ctgttacatt gtcgatctgt tcatggtgaa    2280
cagctttgaa tgcaccaaaa actcgtaaaa gctctgatgt atctatcttt tttacaccgt    2340
tttcatctgt gcatatggac agttttccct ttgatatgta acggtgaaca gttgttctac    2400
ttttgtttgt tagtcttgat gcttcactga tagataccaag agccataaga acctcagatc    2460
cttccgtatt tagccagtat gttctctagt gtggttcgtt gtttttgcgt gagccatgag    2520
aacgaaccat tgagatcatg cttactttgc atgtcactca aaaattttgc ctcaaaactg    2580
gtgagctgaa ttttttgcagt taaagcatcg tgtagtgttt ttcttagtcc gttacgtagg    2640
taggaatctg atgtaatggt tgttggtatt ttgtcaccat tcatttttat ctggttgttc    2700
tcaagttcgg ttacgagatc catttgtcta tctagttcaa cttggaaaat caacgtatca    2760
gtcgggcggc ctcgcttatc aaccaccaat ttcatattgc tgtaagtgtt taaatctta    2820 cttattggtt tcaaaaccca ttggttaagc cttttaaact catggtagtt attttcaagc    2880
attaacatga acttaaattc atcaaggcta atctctatat ttgccttgtg agttttcttt    2940
tgtgttagtt cttttaataa ccactcataa atcctcatag agtatttgtt ttcaaaagac    3000
ttaacatgtt ccagattata ttttatgaat ttttttaact ggaaaagata aggcaatatc    3060
tcttcactaa aaactaattc taattttttcg cttgagaact tggcatagtt tgtccactgg    3120
aaaatctcaa agcctttaac caaaggattc ctgatttcca cagttctcgt catcagctct    3180
ctggttgctt tagctaatac accataagca ttttccctac tgatgttcat catctgagcg    3240
tattggttat aagtgaacga taccgtccgt tctttccttg tagggttttc aatcgtgggg    3300
ttgagtagtg ccacacagca taaaattagc ttggtttcat gctccgttaa gtcatagcga    3360
ctaatcgcta gttcatttgc tttgaaaaca actaattcag acatacatct caattggtct    3420
taggtgatta atcactatac caatggagat gggctagtca atgatattac tagtcctttt    3480
ccttttgagt tgtgggtatc tgtaaattct gctagacctt tgctggaaaa cttgtaaatt    3540
ctgctagacc ctctgtaaat tccgctagac ctttgtgtgt tttttttgtt tatattcaag    3600
tggttataat ttatagaata aagaaagaat aaaaaaagat aaaagaata gatcccagcc    3660 ctgtgtataa ctcactactt tagtcagttc cgcagtatta caaaaggatg tcgcaaacgc    3720
tgtttgctcc tctacaaaac agaccttaaa accctaaagg cttaagtagc accctcgcaa    3780
gctcgggcaa atcgctgaat attccttttg tctccgacca tcaggcacct gagtcgctgt    3840 cttttttcgtg acattcagtt cgctgcgctc acggctctgg cagtgaatgg gggttgtatt    3900
gattcacttg aagtacgaaa aaaaccggga ggacattgga ttattcggga tctgatggga    3960
ttagatttgg tggggcttgc aagcctgtag tgcaaatttt agtcgttaat caatgaaacg    4020
```

```
cgaaagatag taaaaaattg cttttgtttc attgaaaata cgaaaaacaa aaacactgca   4080
aatcatttca ataacagctt caaaaaacgt tcaaaaccga taacaaccaa gctgtcacca   4140
aatgactcat atcacaaatc agcttatgcc gtttaggtat gttacatgtg tgattatgtg   4200
aggtgaagta tgttttagct ggttcatggt tgttatacgg cttttttttac ctcctgtggt   4260
tcctgtgaag gtactacaac actttcctgt tcatgaatcc catactttga caaaatctct   4320
ttgcgttttt cttcaggtaa tgcagtggtc gaaaaaaaaa gcccgcactg tcaggtgcgg   4380
gcttttttct gtgttaagct tgcatgcatt ccaactgcgc taatgacgca gctggacgaa   4440
ggcgggattc tcgtcttacc cgtaggggag gagcaccagt atttgaaacg ggtgcgtcgt   4500
cggggaggcg aatttattat cgataccgtg gaggccgtgc gctttgtccc tttagtgaag   4560
ggtgagctgg cttaaaacgt gaggaaatac ctggattttt cctggttatt ttgccgcagg   4620
tcagcgtata atgaagatct tttccagtgt tgacaagggt gccttgcacg gttataatgt   4680
cactggttat taaccaattt ttcctggggg tcgagatgat tactcactgg gttcgtcagg   4740
gatcttccct gctgggaatg gggctgctgg ttagtctgct gagcggttgt gacacgggcc   4800
aggctaaaaa tgccccgccg ccgccgcccg acgtcagcgt tgcggatgta ttggtgaagc   4860
ctgtcagtca atgggacagc ttcaacgggc gcgttgaagc cgtagaaagc gtgcagctcc   4920
ggcctcgcgt ttcgggttat atcgatagcg ttaattatca tgaaggcgac gaggtcagga   4980
aaggtcaggt cctgtttacc atcgacgatc gcagctaccg tgccgcactg gaacaggcaa   5040
aagcgacgct ggcccgtgcg cgcagtcagg ccagcctgac acgcagcgaa tcggcacgca   5100
ccgagaagct ggtgggtaca caggcggtgt cacgcgagat gtgggaacag cgacgttcga   5160
cagccagtca ggctcaggct gatgtgcagg ccgccgaatc ctctgtcgac atggctcaac   5220
tcaatctgga ttttaccgcg gtcaccgcgc cgattgacgg acgggccagc cgggccatga   5280
ttactgccgg taatcttgtc accgccggcg acagcgccag cgtacttacc acactggttt   5340
cgcaggacaa gatgttcgtc tatttcgacg tcgatgagac caccttcctg cactatcagg   5400
ctatggcacg tcagggacaa cagcggcatg ccctgcccgt tgaaatcggc ctggctggcg   5460
aacagggtta tccacatcgc ggcaacgtcg atttttcttga taaccaactt aatgccagca   5520
ccggtacgat ccgcatgcgc gcccttctgg acaaccgcca gcgcacctat acgcccggcc   5580
tgtttgcccg cgttcgcctt cccggtagcg cgcagtttaa tgccgtgtta atcgacgaca   5640
aagccgtgct gaccgatcag gaccgcaagt atgtctatgt ggtcgatgca cagggtaaag   5700
cccaacgtcg tgatgttcat cccggcgcga tggcggacgg attacgcatc gttaccaccg   5760
gtttacaggc gggcgatcgg gttatcgttg ccggcctgca aaagtgtttt atgcctggta   5820
tgccggtaac ggcaaaaacc gtcgatatgg ccgcgactgc cgcgcgataa cctgaggttg   5880
ttatggattt ttcccgcttt tttattgatc ggccgatctt tgccgccgtg ctgtccgtct   5940
tgatttttat gaccgggctg atcgccatcc cgctgctgcc catcagtgag tatccggacg   6000
tggtgccgcc cagcgtgcag gtgcgtgccg aatatcccgg cgctaacccg aaagccatcg   6060
ccgactccgt ggcaacgccg ctggaagagg cgattaacgg cgttgaaaac atgatgtaca   6120
tgaagtccgt ggccggttct gacggtgtgc tggtgaccac cgtgaccttc cgcccgggta   6180
ccgatccgga tcaggcccag gttcaggtgc aaaaccgcgt agcccaggcc gaggcgcggt   6240
tgccggagga cgtgcgccgt ctcgggatca cgacgcaaaa aatgtcgccg accctgacct   6300
tagtggtgca tctgttttcc cctaataaca cctacgattc gctctatctg cgtaactacg   6360
ccacgctgaa agtcaaagat gagctggccc gtctgccggg cgtggggcaa atccagattt   6420
```

```
ttggcgcggg tgaatacgcg atgcgcgtct ggctcgatcc caacaaagtg gcggcgcgcg    6480
gcttaaccgc ctcggacgtt gtgaaagcga tgcaggagca gaacgtacag gtttctgcgg    6540
ggcaacttgg ggcggaaccg ttaaaaaaac agagcgattt tctgctgtcc attaatatgc    6600
aaggacggct ggaaaacgag cagcagtttg gcgatatcat tctgaaaacg tcagaggacg    6660
gctcactggt ccggctgcgt gacgtggcgc gcattgaaat gggttcaggc agctatgccc    6720
tgcgttcgca gctcaataac aaagacgccg tcggtattgg tatttccag gcaccgggcg     6780 ccaatgctat cgatctgtca aacgcggtgc gtgccaaaat ggatgaactg gccacccgtt    6840
tcccgaacga tgtgaagtgg gctgcgcctt acgatcccac cgtgtttgtt cgcgactcca    6900
ttaaggctgt ggtgcaaacc ctgctggaag cggtgttttt agtggtgctg gtggtgattc    6960
tgttcctgca aacctggcgc gcttccatta ttccctgct ggcggttccg gtatccgtag      7020
tcggcacctt tagcgtgctg tatctgcttg ggttctcgct caacacgcta agcctgttcg    7080
gactggtgct ggccatcggt atcgtggtgg acgatgccat cgtggtggtg gaaaacgttg    7140
aacgcaatat tgagatggga ctgtcaccca aagccgctgc ccatcaggcg atgcgtgagg    7200
tatccggccc gatcattgcc atcgccctcg tgctgtgtgc ggtgttcgtg cccatggcgt    7260
ttctgtcggg cgtgaccggc cagttttaca aacagttcgc caccacgatt gcgatttcaa    7320
ccgtgatctc cgctatcaac tcactgaccc tgtctcccgc actggccgcg atgttactga    7380
aggatcatca ggcccccaaa gatatgccga cgcgcctgat cgacaggctg tttggctgga    7440
ttttccgccc gtttaaccgc ttctttcagc gtagcgcgca cggctatgaa tcgatggtgg    7500
ggaaaaccct gcgtcgtcgc ggcgcggtgt ttggtgttta cctggtgtta ctggctggcg    7560
cgggctggat gtttcatgcg gtgccaggtg ggtttattcc cactcaggac aagctttacc    7620
tgatcggcgg cgtcaaaatg ccggaaggct cgtcgctggc gcgcaccgat gaagtgattc    7680
gtcagatgag cgaaatcggc ctgcaaacgg aaggcgtggc ctatgcggtg gccttccccg    7740
gcctgaacgc gttgcagttt accaatacgc cgaacagcgg cacggtcttt tttggcctga    7800
agccgttccg cgaacgtaaa caaacggcgg cgcagataaa cgcggagatc aatgcgaaaa    7860
tttcccgcat tcaacaggga tttggctttt caattatgcc accgcctatc ctggggctag    7920
gccagggttc gggctattcc ctttacgttc aggatcgggc cggactgggc tatggcgcac    7980
tgcagaccgc gattaacacc ctctcgggcg cggttatgca gacgccgggc atgcacttcc    8040
cgatctcctc ttatcaggcc aacgtgccac agctggaggt gcaggtagac cgcgataagg    8100
cgaaagcaca gggcgtagcg ttaaccgatc tgttcagtac gctacaaact tatctgggtt    8160
catcctacgt taatgacttt aaccgttttg ggcgcacctg gcgcgtgatg gcgcaggcc      8220 acggggaatt ccgcgacagc gttgaggaca tcgcgaacct gcgtacccgt aacgaccgcg    8280
gtgagatggt gccgattggc agcatggtgc atatcaccac ggcctacggc cccgatccgg    8340
tgattcgtta taacggctat ccggcggctg acttgatcgg cgatgccgat ccacgcgtgc    8400
tctcatcggc ccaggcgatg cgtcaacttg aaacgatgtc gggtcagctg ctgccgaacg    8460
gcatgaatat cgaatggacc gatctcagct atcagcaggc gacgcagggt aatacggccc    8520
tgattgtttt ccctgtcgct gtcctgttgg cgttttttagt gctggctgca ctgtatgaga     8580
gctggacgct gccgcttgcg gtgatcctga ttgtgccggt gaccatgctg tctgcccttg    8640
tgggcgtctg gttaaccggt ggggataaca acgtattcgt gcaggttgga ctggtcgtgc    8700
tgatggggct ggcctgtaag aacgccattc tgattgtgga gttcgcccgc gaactggaga    8760
```

```
ttcagggcaa aggcattaca gaagcggcgc tggaagcctg ccgtctgcgc ctgcgtccta    8820
tcgtaatgac ctctatcgcc tttattgccg gcacgatccc cctgattctg ggtgaaggtg    8880
cgggtgctga agtgcgtggc gttaccggcg ttaccgtgtt ctccggtatg ttaggcgtta    8940
cgctgtttgg cttgttcctg acgccggtgt tctacgtgac gctgcgcaag ctggtgacgc    9000
gtaaagccgc tctgcagcgc ttacagaacg cgtcataatc tagaaaacag aatttgcctg    9060
gcggcagtag cgcggtggtc ccacctgacc ccatgccgaa ctcagaagtg aaacgccgta    9120
gcgccgatgg tagtgtgggg tctccccatg cgagagtagg gaactgccag gcatcaaata    9180
aaacgaaagg ctcagtcgaa agactgggcc tttcgtttta tctgttgttt gtcggtgaac    9240
gctctcctga gtaggacaaa tccgccggga gcggatttga acgttgcgaa gcaacggccc    9300
ggagggtggc gggcaggacg cccgccataa actgccaggc atcaaattaa gcagaaggcc    9360
atcctgacgg atggcctttt tgcgtttcta caaactcttc ctgggatcct gcattcgcga    9420
ggtaccgagc tccgctcaag ttagtataaa aagctgaac ggtaaacgta aaatgatata    9480
aatatcaata tattaaatta gattttgcat aaaaaacaga ctacataata ctgtaaaaca    9540
caacatatgc agtcactatg aatcaactac ttagatggta ttagtgacct gtaacagact    9600
gcagctgatg tccggcggtg cttttgccgt tacgcaccac cccgtcagta gctgaacagg    9660
agggacagct gatagaaaca gaagccactg gagcacctca aaaacaccat catacactaa    9720
atcagtaagt tggcagcatc acccgacgca ctttgcgccg aataaatacc tgtgacggaa    9780
gatcacttcg cagaataaat aaatcctggt gtccctgttg ataccgggaa gccctgggcc    9840
aacttttggc gaaatgaga cgttgatcgg cacgtaagag gttccaactt tcaccataat    9900
gaaataagat cactaccggg cgtatttttt gagttatcga ttttcagg agctaaggaa    9960 gctaaaatgg agaaaaaaat cactggatat accaccgttg atatatccca atggcatcgt   10020
aaagaacatt ttgaggcatt tcagtcagtt gctcaatgta cctataacca gaccgttcag   10080
ctggatatta cggcctttt aaagaccgta agaaaaata agcacaagtt tatccggcc    10140 tttattcaca ttcttgcccg cctgatgaat gctcatccgg aattccgtat ggcaatgaaa   10200
gacggtgagc tggtgatatg ggatagtgtt caccttgtt acaccgtttt ccatgagcaa   10260
actgaaacgt tttcatcgct ctggagtgaa taccacgacg atttccggca gtttctacac   10320
atatattcgc aagatgtggc gtgttacggt gaaaacctgg cctatttccc taaagggttt   10380
attgagaata tgttttctcgt ctcagccaat ccctgggtga gtttcaccag ttttgattta   10440
aacgtggcca atatggacaa cttcttcgcc cccgttttca ccatgggcaa atattatacg   10500
caaggcgaca aggtgctgat gccgctggcg attcaggttc atcatgccgt ctgtgatggc   10560
ttccatgtcg gcagaatgct taatgaatta caacagtact gcgatgagtg cagggcggg   10620 gcgtaactcg acgaaatcaa ataatgattt tatttggact gatagtgacc tgttcgttgc   10680
aacaaattga taagcaatgc ttttttataa tgccaactta gtataaaaaa gcaggcttca   10740
agatccccat gtaatgaata aaaagcagta attaatacat ctgtttcatt tgaagcgcga   10800
aagctaaagt tttcgcattt atcgtgaaac gctttcgcgt ttttcgtgcg ccgcttca      10858
```

<210> SEQ ID NO 23
<211> LENGTH: 80
<212> TYPE: DNA
<213> ORGANISM: Artificial Sequence
<220> FEATURE:
<223> OTHER INFORMATION: primer

```
<400> SEQUENCE: 23
ctcatgcggc aatacaacaa caaaaacgca ccgcaattca ggatacaaag tgaagcctgc    60 tttttttatac taagttggca                                              80

<210> SEQ ID NO 24
<211> LENGTH: 80
<212> TYPE: DNA
<213> ORGANISM: Artificial Sequence
<220> FEATURE:
<223> OTHER INFORMATION: primer

<400> SEQUENCE: 24
cggttccggt acggcggtgc agttgctggt atcgtgggtt ttcagctcat cgctcaagtt    60
agtataaaaa agctgaacga                                               80

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
ttgtgctgtt gacggcttca gggtg                                         25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
agcgctgttt ccttgaggga caatc                                         25
```

METHOD FOR PRODUCING L-AMINO ACID

This application is a continuation of, and claims priority under 35 U.S.C. § 119 to Japanese Patent Application No. 2019-012490, filed Jan. 28, 2019, the entireties of which are incorporated by reference herein. Also, the Sequence Listing filed electronically herewith is hereby incorporated by reference (File name: 2020-01-28T_US-604_Seq_List; File size: 46 KB; Date recorded: Jan. 24, 2020).

BACKGROUND

Technical Field

The present invention relates to a method for producing an L-amino acid such as L-glutamic acid by fermentation using a bacterium. L-Amino acids are industrially useful as raw materials for making seasonings and so forth.

Brief Description of the Related Art

L-Amino acids are industrially produced by, for example, fermentation using microorganisms such as bacteria having an L-amino acid-producing ability (Akashi, K. et al., Amino Acid Fermentation. Japan Scientific Societies Press, p. 195 to 215, 1986). As such microorganisms, for example, strains isolated from the nature and mutant strains thereof have been used. Also, an L-amino acid-producing ability of microorganisms can be improved by using recombinant DNA techniques.

The genome sequence of *Pantoea ananatis* AJ13355 has previously been determined and registered as GenBank Accession Number AP012032.2 in NCBI. A c1795 gene was not identified in this genome sequence.

The PAJ_1175 gene of *Pantoea ananatis* AJ13355 are presumed to be a gene encoding a transcriptional regulator belonging to the AraC family based on an analysis using a homology search program BLAST (blast.ncbi.nlm.nih.gov/Blast.cgi). The PAJ_1174 and PAJ_1173 genes of *Pantoea ananatis* AJ13355 are presumed to be genes encoding a periplasm adapter subunit and a permease subunit of a multi-drug efflux transporter belonging to the RND (resistance-nodulation-cell division) superfamily based on an analysis using BLAST, respectively. However, the specific functions of proteins encoded by these genes have not been previously reported.

SUMMARY

An aspect of the present invention is to develop a novel technique for improving an L-amino acid-producing ability of a bacterium, and thereby provide a method for efficiently producing an L-amino acid.

To this end, a novel gene c1795 was found to be located at positions 1401350 to 1401751 in the genome sequence of *Pantoea ananatis* AJ13355 (GenBank Accession Number AP012032.2), and an L-amino acid-producing ability of a bacterium can be improved by modifying this gene. The c1795 gene of *Pantoea ananatis* AJ13355 is presumed to be a gene encoding a transcriptional regulator belonging to the Rrf2 family. In addition, the expression of the PAJ_1175, PAJ_1174, and PAJ_1173 genes were found to be regulated by the c1795 gene, and an L-amino acid-producing ability of a bacterium can be improved by enhancing the expression of the PAJ_1175, PAJ_1174, or PAJ_1173 gene.

It is an aspect of the present invention to provide a bacterium belonging to the family Enterobacteriaceae and having an L-amino acid-producing ability, wherein the bacterium has the feature selected from the group consisting of: (A) the bacterium has been modified so that the activity of a c1795 protein is reduced; and (B) the bacterium has been modified so that the activity of a protein P is increased, wherein the expression of protein P is repressed by a c1795 protein.

It is a further aspect of the present invention to provide the bacterium as described above, wherein the protein P is a protein selected from the group consisting of a PAJ_1175 protein, a PAJ_1174 protein, a PAJ_1173 protein, and combinations thereof.

It is a further aspect of the present invention to provide the bacterium as described above, wherein at least the activity of the PAJ_1175 protein is increased, or at least the activities of the PAJ_1174 protein and PAJ_1173 protein are increased.

It is a further aspect of the present invention to provide the bacterium as described above, wherein the activity of the protein P is increased by increasing the expression of a gene encoding the protein P.

It is a further aspect of the present invention to provide the bacterium as described above, wherein the expression of the gene encoding the protein P is increased by a method selected from the group consisting of: (1) increasing the copy number of the gene encoding the protein P; (2) modifying an expression control sequence of the gene encoding the protein P; (3) reducing the activity of the c1795 protein; and (4) combinations thereof.

It is a further aspect of the present invention to provide the bacterium as described above, wherein the activity of the c1795 protein is reduced by reducing the expression of a c1795 gene and/or disrupting a c1795 gene.

It is a further aspect of the present invention to provide the bacterium as described above, wherein the expression of the c1795 gene is reduced by modifying an expression control sequence of the c1795 gene.

It is a further aspect of the present invention to provide the bacterium as described above, wherein the activity of the c1795 protein is reduced by deleting a partial or the entire region of the amino acid sequence of the c1795 protein.

It is a further aspect of the present invention to provide the bacterium as described above, wherein the activity of the c1795 protein is reduced by a method selected from the group consisting of: A) deletion of a partial or the entire region of the coding region of the c1795 gene, B) introduction of a stop codon into the coding region of the c1795 gene, C) introduction of a frame shift into the coding region of the c1795 gene, and D) combinations thereof.

It is a further aspect of the present invention to provide the bacterium as described above, wherein the c1795 protein is selected from the group consisting of: (a) a protein comprising the amino acid sequence of SEQ ID NO: 2; (b) a protein comprising the amino acid sequence of SEQ ID NO: 2, but which includes substitution, deletion, insertion, and/or addition of 1 to 10 amino acid residues, and having a function of a c1795 protein; and (c) a protein comprising an amino acid sequence having an identity of 90% or higher to the amino acid sequence of SEQ ID NO: 2, and having a function of a c1795 protein.

It is a further aspect of the present invention to provide the bacterium as described above, wherein the PAJ_1175 protein is: (a) a protein comprising the amino acid sequence of SEQ ID NO: 4; (b) a protein comprising the amino acid sequence of SEQ ID NO: 4, but which includes substitution, deletion, insertion, and/or addition of 1 to 10 amino acid residues, and having a function of a PAJ_1175 protein; and (c) a protein comprising an amino acid sequence having an identity of 90% or higher to the amino acid sequence of SEQ ID NO: 4, and having a function of a PAJ_1175 protein.

It is a further aspect of the present invention to provide the bacterium as described above, wherein the PAJ_1174 protein is selected from the group consisting of: (a) a protein comprising the amino acid sequence of SEQ ID NO: 6; (b) a protein comprising the amino acid sequence of SEQ ID NO: 6, but which includes substitution, deletion, insertion, and/or addition of 1 to 10 amino acid residues, and having a function of a PAJ_1174 protein; and (c) a protein comprising an amino acid sequence having an identity of 90% or higher to the amino acid sequence of SEQ ID NO: 6, and having a function of a PAJ_1174 protein.

It is a further aspect of the present invention to provide the bacterium as described above, wherein the PAJ_1173 protein is selected from the group consisting of: (a) a protein comprising the amino acid sequence of SEQ ID NO: 8; (b) a protein comprising the amino acid sequence of SEQ ID NO: 8, but which includes substitution, deletion, insertion, and/or addition of 1 to 10 amino acid residues, and having a function of a PAJ_1173 protein; and (c) a protein comprising an amino acid sequence having an identity of 90% or higher to the amino acid sequence of SEQ ID NO: 8, and having a function of a PAJ_1173 protein.

It is a further aspect of the present invention to provide the bacterium as described above, wherein the bacterium is a *Pantoea* bacterium or an *Escherichia* bacterium.

It is a further aspect of the present invention to provide the bacterium as described above, wherein the bacterium is *Pantoea ananatis* or *Escherichia coli*.

It is a further aspect of the present invention to provide a method for producing an L-amino acid, the method comprising: culturing the bacterium as described above in a medium to accumulate the L-amino acid in the medium and/or cells of the bacterium; and collecting the L-amino acid from the medium and/or the cells.

It is a further aspect of the present invention to provide the method as described above, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

It is a further aspect of the present invention to provide the method as described above, wherein the L-amino acid is selected from the group consisting of L-glutamic acid, L-lysine, L-threonine, L-tryptophan, and combinations thereof.

It is a further aspect of the present invention to provide the method as described above, wherein the L-amino acid is L-glutamic acid.

It is a further aspect of the present invention to provide the method as described above, wherein the L-glutamic acid is monoammonium L-glutamate or monosodium L-glutamate.

According to the present invention, an L-amino acid-producing ability of a bacterium can be improved, and an L-amino acid can be efficiently produced.

DETAILED DESCRIPTION

The method as described herein is a method for producing an L-amino acid which includes the steps of culturing a bacterium belonging to the family Enterobacteriaceae and having an L-amino acid-producing ability in a medium to accumulate an L-amino acid in the medium and/or cells of the bacterium, and collecting the L-amino acid from the medium and/or cells of the bacterium, wherein the bacterium has been modified so as to have a specific feature. The bacterium useful in this method can also be referred to as the "bacterium of the present invention".

<1> Bacterium

The bacterium as described herein is a bacterium that belongs to the family Enterobacteriaceae and is able to produce an L-amino acid, wherein the bacterium has been modified so as to have the specific feature.

<1-1> Bacterium Having L-Amino Acid-Producing Ability

The phrase "bacterium having an L-amino acid-producing ability" can refer to a bacterium having an ability to generate and accumulate an objective L-amino acid in a medium and/or cells of the bacterium to such a degree that the L-amino acid can be collected, when the bacterium is cultured in the medium. The bacterium having an L-amino acid-producing ability may be a bacterium that is able to accumulate an objective L-amino acid in a medium and/or cells of the bacterium in an amount larger than that obtainable with a non-modified strain. The term "non-modified strain" can refer to a control strain that has not been modified so as to have the specific feature. That is, examples of the non-modified strain include a wild-type strain and parental strain. The bacterium having an L-amino acid-producing ability may be a bacterium that is able to accumulate an objective L-amino acid in a medium in an amount of 0.5 g/L or more, or 1.0 g/L or more.

Examples of the L-amino acid include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. Particular examples of the L-amino acid include L-glutamic acid, L-lysine, L-threonine, L-arginine, L-histidine, L-isoleucine, L-valine, L-leucine, L-phenylalanine, L-tyrosine, L-tryptophan, and L-cysteine. More particular examples of the L-amino acid include L-glutamic acid, L-lysine, L-threonine, and L-tryptophan. More particular examples of the L-amino acid include L-glutamic acid. Particular examples of the L-amino acid also include L-amino acids of glutamate family. The term "L-amino acid of glutamate family" collectively refers to L-glutamic acid and L-amino acids that are biosynthesized via L-glutamic acid as an intermediate. Examples of the L-amino acids that are biosynthesized via L-glutamic acid as an intermediate include L-glutamine, L-proline, L-arginine, L-citrulline, and L-ornithine. The bacterium may have an ability to produce one kind of L-amino acid, or two or more kinds of L-amino acids.

The term "amino acid" can refer to an L-amino acid, unless otherwise stated. The term "L-amino acid" can refer to an L-amino acid in a free form, a salt thereof, or a mixture thereof, unless otherwise stated. Examples of salts are described herein.

Examples of bacteria belonging to the family Enterobacteriaceae include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database can be used.

The *Escherichia* bacteria are not particularly limited, and examples thereof include those classified into the genus *Escherichia* according to the taxonomy known to those skilled in the field of microbiology. Examples of the *Escherichia* bacteria include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria include, for example, *Escherichia coli*. Specific examples of *Escherichia coli* include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof.

The *Enterobacter* bacteria are not particularly limited, and examples include those classified into the genus *Enterobacter* according to the taxonomy known to those skilled in the field of microbiology. Examples of the *Enterobacter* bacterium include, for example, *Enterobacter agglomerans* and *Enterobacter aerogenes*. Specific examples of *Enterobacter agglomerans* include, for example, the *Enterobacter agglomerans* ATCC 12287 strain. Specific examples of *Enterobacter aerogenes* include, for example, the *Enterobacter aerogenes* ATCC 13048 strain, NBRC 12010 strain (Biotechnol. Bioeng., 2007 Mar. 27; 98(2):340-348), and AJ110637 strain (FERM BP-10955). Examples of the *Enterobacter* bacteria also include, for example, the strains described in European Patent Application Laid-open (EP-A) No. 0952221. In addition, *Enterobacter agglomerans* also include some strains classified as *Pantoea agglomerans*.

The *Pantoea* bacteria are not particularly limited, and examples include those classified into the genus *Pantoea* according to the taxonomy known to those skilled in the field of microbiology. Examples of the *Pantoea* bacteria include, for example, *Pantoea ananatis, Pantoea stewartii, Pantoea agglomerans*, and *Pantoea citrea*. Specific examples of *Pantoea ananatis* include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some of *Enterobacter* bacteria and *Erwinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Int. J. Syst. Bacteriol., 39, 337-345 (1989)). The *Pantoea* bacteria include those reclassified into the genus *Pantoea* as described above.

Examples of the *Erwinia* bacteria include *Erwinia amylovora* and *Erwinia carotovora*. Examples of the *Klebsiella* bacteria include *Klebsiella planticola*.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

The bacterium may be a bacterium inherently having an L-amino acid-producing ability, or may be a bacterium modified so that it has an L-amino acid-producing ability. The bacterium having an L-amino acid-producing ability can be obtained by imparting an L-amino acid-producing ability to such a bacterium as mentioned above, or by enhancing an L-amino acid-producing ability of such a bacterium as mentioned above.

To impart or enhance an L-amino acid-producing ability, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of an L-amino acid biosynthetic enzyme may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a usual mutagenesis treatment, and then selecting a strain exhibiting autotrophy, analogue resistance, or a metabolic regulation mutation, and having an L-amino acid-producing ability from the obtained mutant strains. Examples of the usual mutagenesis treatment include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP1010755A, and so forth. The detailed procedures for enhancing enzyme activity are described herein.

Furthermore, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" referred to herein includes an enzyme involved in decomposition of the objective amino acid. The method for reducing an enzyme activity are described herein.

Hereinafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability include, for example, a method of modifying a bacterium so that the bacterium has an increased activity or activities of one or more of the L-glutamic acid biosynthesis enzymes. Examples of such enzymes include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (gltA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are examples of genes encoding the enzymes (the same shall apply to the same occasions hereinafter). It is a particular example to enhance the activity or activities of one or more of, for example, glutamate dehydrogenase, citrate synthase, phosphoenol pyruvate carboxylase, and methylcitrate synthase, among these enzymes.

Examples of strains belonging to the family Enterobacteriaceae and modified so that the expression of the citrate synthase gene, phosphoenolpyruvate carboxylase gene, and/or glutamate dehydrogenase gene are increased include those disclosed in EP1078989A, EP955368A, and EP952221A. Furthermore, examples of strains belonging to the family Enterobacteriaceae and modified so that the expression of a gene of the Entner-Doudoroff pathway (edd, eda) is increased include those disclosed in EP1352966B.

Examples of methods for imparting or enhancing L-glutamic acid-producing ability also include, for example, a method of modifying a bacterium so that the bacterium has a reduced activity or activities of one or more enzymes that catalyze a reaction branching away from the biosynthesis pathway of L-glutamic acid to generate a compound other than L-glutamic acid. Examples of such enzymes include, but are not particularly limited to, isocitrate lyase (aceA), α-ketoglutarate dehydrogenase (sucA), acetolactate synthase (ilvI), formate acetyltransferase (pfZ), lactate dehydrogenase (ldh), alcohol dehydrogenase (adh), glutamate decarboxylase (gadAB), and succinate dehydrogenase (sdhABCD). It is a particular example to reduce or delete, for example, the α-ketoglutarate dehydrogenase activity, among these enzymes.

*Escherichia* bacteria having a reduced α-ketoglutarate dehydrogenase activity or are deficient in the α-ketoglutarate dehydrogenase activity, and methods for obtaining them are described in U.S. Pat. Nos. 5,378,616 and 5,573,945. Furthermore, methods for reducing or deleting the α-ketoglutarate dehydrogenase activity of Enterobacteriaceae bacteria such as *Pantoea* bacteria, *Enterobacter* bacteria, *Klebsiella* bacteria, and *Erwinia* bacteria are disclosed in U.S. Pat. Nos. 6,197,559, 6,682,912, 6,331,419, and 8,129,151, and WO2008/075483. Specific examples of *Escherichia* bacteria having a reduced α-ketoglutarate dehydrogenase activity or are deficient in the α-ketoglutarate dehydrogenase activity include the following strains:

E. *coli* W3110sucA::Km$^r$
E. *coli* AJ12624 (FERM BP-3853)
E. *coli* AJ12628 (FERM BP-3854)
E. *coli* AJ12949 (FERM BP-4881)

E. *coli* W3110sucA::Km$^r$ is a strain obtained by disrupting the sucA gene encoding α-ketoglutarate dehydrogenase of E. *coli* W3110. This strain is completely deficient in α-ketoglutarate dehydrogenase activity.

Examples of L-glutamic acid-producing bacteria and parental strains that can be used to derive them also include *Pantoea* bacteria, such as the *Pantoea ananatis* AJ13355 strain (FERM BP-6614), *Pantoea ananatis* SC17 strain (FERM BP-11091), and *Pantoea ananatis* SC17(0) strain (VKPM B-9246). The AJ13355 strain is a strain isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depository (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614. The strain SC17(0) was deposited in the Russian National Collection of Industrial Microorganisms (VKPM; FGUP GosNII Genetika, Russian Federation, 117545 Moscow, 1st Dorozhny proezd, 1) on Sep. 21, 2005 under the accession number VKPM B-9246.

Furthermore, examples of L-glutamic acid-producing bacteria and parental strains that can be used to derive them also include *Pantoea* bacteria having a reduced α-ketoglutarate dehydrogenase activity or are deficient in the α-ketoglutarate dehydrogenase activity. Examples of such strains include the AJ13356 strain (U.S. Pat. No. 6,331,419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, under an accession number of FERM BP-8646.

The AJ13355 strain was identified as *Enterobacter agglomerans* when it was isolated, but it was recently reclassified as *Pantoea ananatis* on the basis of nucleotide sequencing of 16S rRNA and so forth. Therefore, although the AJ13355 and AJ13356 strains are deposited at the aforementioned depository as *Enterobacter agglomerans*, and they are referred to as *Pantoea ananatis* in this specification.

Furthermore, examples of L-glutamic acid-producing bacteria and parent strains that can be used to derive them also include *Pantoea* bacteria such as the *Pantoea ananatis* SC17sucA/RSFCPG+pSTVCB strain, *Pantoea ananatis* AJ13601 strain, *Pantoea ananatis* NP106 strain, and *Pantoea ananatis* NA1 strain. The SC17sucA/RSFCPG+pSTVCB strain is a strain obtained by introducing into the SC17sucA strain a plasmid RSFCPG, which contains a citrate synthase gene (gltA), phosphoenolpyruvate carboxylase gene (ppc), and glutamate dehydrogenase gene (gdhA) derived from *Escherichia coli*, and a plasmid pSTVCB, which contains a citrate synthase gene (gltA) derived from *Brevibacterium lactofermentum*. The AJ13601 strain is a strain selected from the SC17sucA/RSFCPG+pSTVCB strain as a strain resistant to a high concentration of L-glutamic acid at a low pH. The NP106 strain is a strain obtained from the AJ13601 strain by curing the plasmids RSFCPG and pSTVCB. The NA1 strain is a strain obtained by introducing a plasmid RSFPPG into the NP106 strain (WO2010/027045). The plasmid RSFPPG has a structure in which the gltA gene of the plasmid RSFCPG was replaced with a methylcitrate synthase gene (prpC), and that is, contains the prpC gene, ppc gene, and gdhA gene (WO2008/020654). The AJ13601 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parent strains that can be used to derive them also include strains in which both the α-ketoglutarate dehydrogenase (sucA) activity and the succinate dehydrogenase (sdh) activity are reduced or deleted (Japanese Patent Laid-open (Kokai) No. 2010-041920). Specific examples of such strains include, for example, a sucAsdhA double-deficient strain of the *Pantoea ananatis* NA1 strain (Japanese Patent Laid-open (Kokai) No. 2010-041920).

Examples of L-glutamic acid-producing bacteria and parental strains that can be used to derive them also include auxotrophic mutant strains. Specific examples of auxotrophic mutant strains include, for example, *E. coli* VL334thrC$^+$ (VKPM B-8961, EP1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC$^+$ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parental strains that can be used to derive them also include strains having resistance to an aspartic acid analogue. Such strains can also be deficient in the α-ketoglutarate dehydrogenase activity. Specific examples of strains having resistance to an aspartic acid analogue and deficient in the α-ketoglutarate dehydrogenase activity include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* AJ13138 (FERM BP-5565, U.S. Pat. No. 6,110,714).

Examples of methods for imparting or enhancing L-glutamic acid-producing ability also include, for example, a method of enhancing the expression of an L-glutamic acid secretion gene, such as yhfK gene (WO2005/085419) or ybjL gene (WO2008/133161).

The methods for imparting or enhancing L-glutamic acid-producing ability can also be effective for imparting or enhancing an ability to produce L-amino acids that are biosynthesized via L-glutamic acid as an intermediate, such as L-glutamine, L-proline, L-arginine, L-citrulline, and L-ornithine. Hence, a bacterium having an ability to produce any of these L-amino acids that are biosynthesized via L-glutamic acid may have, as required, such a property possessed by an L-glutamic acid-producing bacterium as described above. For example, a bacterium having an ability to produce any of these L-amino acids that are biosynthesized via L-glutamic acid may be modified so that the activity of α-ketoglutarate dehydrogenase and/or succinate dehydrogenase is reduced.

<L-Glutamine-Producing Bacteria>

Examples of the method for imparting or enhancing L-glutamine-producing ability include, for example, a method of modifying a bacterium so that the activity or activities of one or more of the L-glutamine biosynthesis enzymes are enhanced. Examples of such enzymes include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP1229121).

Examples of the method for imparting or enhancing L-glutamine-producing ability also include, for example, a method of modifying a bacterium so that the activity or activities of one or more enzymes that catalyze a reaction branching away from the biosynthesis pathway of L-glutamine to generate a compound other than L-glutamine are reduced. Examples of such enzymes include, but are not particularly limited to, glutaminase.

Specific examples of L-glutamine-producing bacteria and parent strains that can be used to derive them include, for example, a strain belonging to the genus *Escherichia* and having a mutant glutamine synthetase in which the tyrosine residue of the position 397 of glutamine synthetase has been replaced with another amino acid residue (US2003-0148474A).

<L-Proline-Producing Bacteria>

Examples of methods for imparting or enhancing L-proline-producing ability include, for example, a method of modifying a bacterium so that the bacterium has an increased activity or activities of one or more of the L-proline biosynthesis enzymes. Examples of such enzymes include glutamate-5-kinase (proB), γ-glutamylphosphate reductase, and pyroline-5-carboxylate reductase (putA). For enhancing the activity of such an enzyme, for example, the proB gene encoding a glutamate-5-kinase desensitized to feedback inhibition by L-proline (German Patent No. 3127361) can be used.

Examples of methods for imparting or enhancing L-proline-producing ability also include, for example, a method of modifying a bacterium so that the bacterium has a reduced activity of an enzyme involved in decomposition of L-proline. Examples of such an enzyme include proline dehydrogenase and ornithine aminotransferase.

Specific examples of L-proline-producing bacteria and parental strains that can be used to derive them include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 strain (VKPM B-8011), which is a 3,4-dehydroxyproline and azetidine-2-carboxylate resistant strain, and *E. coli* 702ilvA strain (VKPM B-8012), which is an ilvA gene-deficient strain of the 702 strain (EP1172433).

<L-Threonine-Producing Bacteria>

Examples of methods for imparting or enhancing L-threonine-producing ability include, for example, a method of modifying a bacterium so that the bacterium has an increased activity or activities of one or more of the L-threonine biosynthesis enzymes. Examples of such enzymes include, but are not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, it is a particular example to enhance activity or activities of aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine. Examples of such a strain in which threonine decomposition is suppressed include, for example, the *E. coli* TDH6 strain, which is deficient in threonine dehydrogenase activity (Japanese Patent Laid-open (Kokai) No. 2001-346578).

The activities of the L-threonine biosynthesis enzymes are inhibited by the end product, L-threonine. Therefore, for constructing L-threonine-producing strains, it is a particular example that the genes of the L-threonine biosynthesis enzymes are modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture broth and also suppressed by attenuation. Therefore, expression of the threonine operon can be enhanced by removing the leader sequence or the attenuator in the attenuation region (Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is present upstream of the threonine operon, and can be replaced with a non-native promoter (WO98/04715). Also, the threonine operon may be constructed so that the threonine biosynthesis genes are expressed under control of the repressor and promoter of λ-phage (EP0593792B). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

The expression amount of the threonine operon that is modified so as to be desensitized to feedback inhibition by L-threonine as described above can be increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance include the rhtA gene (Res. Microbiol. 154:123-135 (2003)), rhtB gene (EP0994190A), rhtC gene (EP1013765A), yfiK gene, and yeaS gene (EP1016710A). Methods for imparting L-threonine resistance to a host are described in EP0994190A and WO90/04636, for example.

Specific examples of L-threonine-producing bacteria and parental strains that can be used to derive them include, for example, *E. coli* TDH-6/pVIC40 (VKPM B-3996, U.S. Pat. Nos. 5,175,107 and 5,705,371), *E. coli* 472T23/pYN7 (ATCC 98081, U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP1149911A), and *E. coli* VKPM B-5318 (EP0593792B).

The VKPM B-3996 strain is obtained by introducing the plasmid pVIC40 into the TDH-6 strain. The TDH-6 strain has sucrose-assimilating ability, is deficient in the thrC gene, and the ilvA gene thereof has a leaky mutation. The TDH-6 strain also has a mutation in the rhtA gene, which imparts resistance to high concentration of threonine or homoserine. The plasmid pVIC40 is a plasmid obtained by inserting the thrA*BC operon containing a mutant thrA gene encoding an aspartokinase-homoserine dehydrogenase I resistant to feedback inhibition by threonine and the wild-type thrBC genes into an RSF 1010-derived vector (U.S. Pat. No. 5,705,371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 in which the regulatory region of the threonine operon is replaced with the temperature-sensitive λ-phage Cl repressor and PR promoter. The VKPM B-5318 strain was deposited at the Russian National Collection of Industrial Microorganisms (VKPM, FGUP GosNII Genetika, 1 Dorozhny proezd., 1 Moscow 117545, Russia) on May 3, 1990 under the accession number of VKPM B-5318.

The thrA gene which encodes aspartokinase-homoserine dehydrogenase I of *E. coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC_000913.2, gi: 49175990). The thrB gene is located between the thrA and thrC genes on the chromosome of *E. coli* K-12. The thrC gene which encodes threonine synthase of *E. coli* has been elucidated (nucleotide numbers 3734 to 5020, GenBank accession NC_000913.2, gi: 49175990). The thrC gene is located between the thrB gene and the yaaX open reading frame on the chromosome of *E. coli* K-12. The thrA*BC operon containing a mutant thrA gene which encodes an aspartokinase-homoserine dehydrogenase I resistant to feedback inhibition by threonine and the wild-type thrBC genes can be obtained from the well-known plasmid pVIC40, which is present in the threonine-producing *E. coli* strain VKPM B-3996 (U.S. Pat. No. 5,705,371).

The rhtA gene of *E. coli* is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The gene unit expressing a protein encoded by the ORF1 has been designated rhtA (rht: resistance to homoserine and threonine). It has also been revealed that the rhtA23 mutation that imparts resistance to high concentration of threonine or homoserine is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457; EP1013765A).

The asd gene of *E. coli* has already been elucidated (nucleotide numbers 3572511 to 3571408, GenBank accession NC_000913.1, gi:16131307), and can be obtained by PCR (White, T. J., et al., Trends Genet, 5:185-189, 1989) utilizing primers prepared on the basis of the nucleotide sequence of the gene. The asd genes of other microorganisms can also be obtained in a similar manner.

The aspC gene of *E. coli* has also previously been elucidated (nucleotide numbers 983742 to 984932, GenBank accession NC_000913.1, gi:16128895), and can be obtained by PCR utilizing primers prepared on the basis of the nucleotide sequence of the gene. The aspC genes of other microorganisms can also be obtained in a similar manner.

<L-Lysine-Producing Bacteria>

Examples of methods for imparting or enhancing L-lysine-producing ability include, for example, a method of modifying a bacterium so that the bacterium has an increased activity or activities of one or more of the L-lysine biosynthesis enzymes. Examples of such enzymes include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195A). It is a particular example to enhance the activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase, among these enzymes. Furthermore, L-lysine-producing bacteria and parental strains that can be used to derive them can express an increased level of the gene involved in energy efficiency (cyo) (EP1170376A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Examples of the aspartokinase III desensitized to feedback inhibition by L-lysine include aspartokinase III derived from *Escherichia coli* and having one or more of the following mutations: replacing the methionine residue at position 318 with an isoleucine residue; replacing the glycine residue at position 323 with an aspartic acid residue; and replacing the threonine residue at position 352 with an isoleucine residue (U.S. Pat. Nos. 5,661,012 and 6,040,160). Furthermore, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme. Examples of the dihydrodipicolinate synthase desensitized to feedback inhibition by L-lysine include dihydrodipicolinate synthase derived from *Escherichia coli* and having a mutation for replacing the histidine residue at position 118 with a tyrosine residue (U.S. Pat. No. 6,040,160).

Examples of methods for imparting or enhancing L-lysine-producing ability also include, for example, a method of modifying a bacterium so that the bacterium has a reduced activity or activities of one or more enzymes that catalyze a reaction branching away from the biosynthetic pathway of L-lysine to generate a compound other than L-lysine. Examples of such enzymes include, but are not particularly limited to, homoserine dehydrogenase, lysine decarboxylase (U.S. Pat. No. 5,827,698), and malic enzyme (WO2005/010175).

Examples of L-lysine-producing bacteria and parental strains that can be used to derive them also include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues include, but are not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of L-lysine-producing bacteria and parental strains that can be used to derive them include *E. coli* AJ11442 (FERM BP-1543, NRRL B-12185, U.S. Pat. No. 4,346,170) and *E. coli* VL611. In these strains, aspartokinase is desensitized to feedback inhibition by L-lysine.

Specific examples of L-lysine-producing bacteria and parental strains that can be used to derive them also include the *E. coli* WC196 strain. The WC196 strain was bred by imparting AEC resistance to the W3110 strain, which was derived from *E. coli* K-12 (U.S. Pat. No. 5,827,698). The WC196 strain was designated *E. coli* AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Examples of L-lysine-producing bacteria include *E. coli* WC196ΔcadAΔldc and *E. coli* WC196ΔcadAΔldc/pCABD2 (WO2010/061890). The *E. coli* WC196ΔcadAΔldc is a strain constructed from the WC196 strain by disrupting the cadA and ldcC genes encoding lysine decarboxylase. The WC196ΔcadAΔldc/pCABD2 strain was constructed by introducing the plasmid pCABD2 containing lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from *Escherichia coli* and encoding a dihydrodipicolinate synthase (DDPS) having a mutation for desensitization to feedback inhibition by L-lysine (H118Y), a mutant lysC gene derived from *Escherichia coli* and encoding aspartokinase III having a mutation for desensitization to feedback inhibition by L-lysine (T352I), the dapB gene derived from *Escherichia coli* and encoding dihydrodipicolinate reductase, and the ddh gene derived from *Brevibacterium lactofermentum* and encoding diaminopimelate dehydrogenase.

Examples of L-lysine-producing bacteria also include *E. coli* AJIK01 (NITE BP-01520). The AJIK01 strain was designated *E. coli* AJ111046, and deposited at the independent administrative agency, National Institute of Technology and Evaluation, Patent Microorganisms Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

<L-Arginine-Producing Bacteria>

Examples of methods for imparting or enhancing L-arginine-producing ability include, for example, a method of modifying a bacterium so that the bacterium has an increased activity or activities of one or more of the L-arginine biosynthesis enzymes. Examples of such enzymes include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), argininosuccinate synthetase (argG), argininosuccinate lyase (argH), ornithine acetyl transferase (argJ), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (EP1170361A) can be used.

Specific examples of L-arginine-producing bacteria and parental strains that can be used to derive them include, for example, the *E. coli* 237 strain (VKPM B-7925, US2002-058315A1), derivative strains thereof introduced with the argA gene encoding a mutant N-acetyl glutamate synthase (Russian Patent Application No. 2001112869, EP1170361A1), *E. coli* 382 strain derived from the 237 strain and having an improved acetic acid-assimilating ability (VKPM B-7926, EP1170358A1), and *E. coli* 382ilvA+ strain, which is a strain obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under accession number of VKPM B-7926.

Examples of L-arginine-producing bacteria and parental strains that can be used to derive them also include strains having resistance to amino acid analogues, and so forth. Examples of such strains include *E. coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (Japanese Patent Laid-open (Kokai) No. 56-106598).

<L-Citrulline-Producing Bacteria and L-Ornithine-Producing Bacteria>

L-citrulline and L-ornithine are intermediates of the biosynthetic pathway of L-arginine. Hence, examples of methods for imparting or enhancing an ability to produce L-citrulline and/or L-ornithine include, for example, a method of modifying a bacterium so that the bacterium has an increased activity or activities of one or more of the L-arginine biosynthesis enzymes. Examples of such enzymes include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), ornithine acetyl transferase (argJ), and carbamoyl phosphate synthetase (carAB), for L-citrulline. Furthermore, examples of such enzymes include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), and ornithine acetyl transferase (argJ), for L-ornithine.

An L-citrulline-producing bacterium can be easily obtained from, for example, an L-arginine bacterium such as the *E. coli* 382 strain (VKPM B-7926) by reducing the activity of argininosuccinate synthetase encoded by argG gene. Also, an L-ornithine-producing bacterium can be easily obtained from, for example, an L-arginine bacterium such as the *E. coli* 382 strain (VKPM B-7926) by reducing the activity of ornithine carbamoyl transferase encoded by argF and argI genes.

Specific examples of L-citrulline-producing bacteria and parental strains that can be used to derive them include, for example, strains belonging to the genus *Escherichia*, such as the *E. coli* strains 237/pMADS11, 237/pMADS12, and 237/pMADS13, which have a mutant N-acetylglutamate synthase (Russian patent No. 2,215,783, U.S. Pat. No. 6,790,647, and EP1170361B1), *E. coli* strains 333 (VKPM B-8084) and 374 (VKPM B-8086), which have carbamoyl phosphate synthetase resistant to feedback inhibition (Russian patent No. 2,264,459), and *E. coli* strains having an increased activity of α-ketoglutarate synthase and having a modified activity of ferredoxin NADP$^+$ reductase, pyruvate synthase, and/or α-ketoglutarate dehydrogenase (EP2133417A). Specific examples of L-citrulline-producing bacteria and parental strains that can be used to derive them also include, for example, strains belonging to the genus *Pantoea*, such as the *P. ananatis* NA1sucAsdhA strain, which has reduced activities of succinate dehydrogenase and α-ketoglutarate dehydrogenase (US2009-286290A1).

<L-Histidine-Producing Bacteria>

Examples of methods for imparting or enhancing L-histidine-producing ability include, for example, a method of modifying a bacterium so that the bacterium has an increased activity or activities of one or more of the L-histidine biosynthesis enzymes. Examples of such enzymes include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2,003,677 and 2,119,536).

Specific examples of L-histidine-producing bacteria and parental strains that can be used to derive them include, for example, strains belonging to the genus *Escherichia*, such as the *E. coli* 24 strain (VKPM B-5945, RU2003677), *E. coli* NRRL B-12116 to B-12121 (U.S. Pat. No. 4,388,405), *E. coli* H-9342 (FERM BP-6675) and H-9343 (FERM BP-6676, U.S. Pat. No. 6,344,347), *E. coli* H-9341 (FERM BP-6674, EP1085087), *E. coli* AI80/pFM201 (U.S. Pat. No. 6,258,554), *E. coli* FERM P-5038 and FERM P-5048, which have been introduced with a vector carrying a DNA encoding an L-histidine-biosynthesis enzyme (Japanese Patent Laid-open (Kokai) No. 56-005099), *E. coli* strains introduced with a gene for amino acid transport (EP1016710A), and *E. coli* 80 strain, which has been imparted with resistance to sulfaguanidine, DL-1,2,4-triazole-3-alanine, and streptomycin (VKPM B-7270, Russian Patent No. 2119536).

<L-Cysteine-Producing Bacteria>

Examples of methods for imparting or enhancing L-cysteine-producing ability include, for example, a method of modifying a bacterium so that the bacterium has an increased activity or activities of one or more of the L-cysteine biosynthesis enzymes. Examples of such enzymes include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and US2005-0112731A. Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of methods for imparting or enhancing L-cysteine-producing ability also include, for example, a method of modifying a bacterium so that the bacterium has a reduced activity or activities of one or more of the enzymes that catalyze a reaction branching away from the biosynthesis pathway of L-cysteine to generate a compound other than L-cysteine. Examples of such enzymes include, for example, enzymes involved in decomposition of L-cysteine. Examples of the enzymes involved in decomposition of L-cysteine include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), O-acetylserine sulfhydrylase B (cysM, Japanese Patent Laid-open (Kokai) No. 2005-245311), the malY gene product (Japanese Patent Laid-open (Kokai) No. 2005-245311), the d0191 gene product of *Pantoea ananatis* (Japanese Patent Laid-open (Kokai) No. 2009-232844), and cysteine desulfhydrase (aecD, Japanese Patent Laid-open (Kokai) No. 2002-233384.

Furthermore, examples of methods for imparting or enhancing L-cysteine-producing ability also include, for example, a method of enhancing the L-cysteine excretory system, and a method of enhancing the sulfate/thiosulfate transport system. Examples of proteins of the L-cysteine excretory system include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojlH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system include the proteins encoded by the cysPTWAM gene cluster.

Specific examples of L-cysteine-producing bacteria and parental strains that can be used to derive them include, for example, *E. coli* JM15 transformed with different cysE alleles encoding feedback-resistant serine acetyltransferases (U.S. Pat. No. 6,218,168, Russian patent application 2003121601), *E. coli* W3110 having an over-expressed gene encoding a protein suitable for secretion of a cytotoxic substance (U.S. Pat. No. 5,972,663), *E. coli* strains having a reduced cysteine desulfohydrase activity (Japanese Patent Laid-open (Kokai) No. 11-155571), and *E. coli* W3110 having an increased activity of a positive transcriptional regulator for cysteine regulon encoded by the cysB gene (WO01/27307A1).

<L-Methionine-Producing Bacteria>

Examples of L-methionine-producing bacteria and parental strains that can be used to derive them include L-threonine auxotrophic strains and mutant strains resistant to norleucine (Japanese Patent Laid-open (Kokai) No. 2000-139471). Examples of L-methionine-producing bacteria and parental strains that can be used to derive them also include a strain containing a mutant homoserine transsuccinylase resistant to feedback inhibition by L-methionine (Japanese Patent Laid-open (Kokai) No. 2000-139471, US2009-0029424A). Since L-methionine is biosynthesized via L-cysteine as an intermediate, L-methionine-producing ability can also be improved by improving L-cysteine-producing ability (Japanese Patent Laid-open (Kokai) No. 2000-139471, US2008-0311632A).

Specific examples of L-methionine-producing bacteria and parental strains that can be used to derive them include, for example, E. coli AJ11539 (NRRL B-12399), E. coli AJ11540 (NRRL B-12400), E. coli AJ11541 (NRRL B-12401), E. coli AJ11542 (NRRL B-12402, British Patent No. 2075055), the E. coli 218 strain (VKPM B-8125, Russian Patent No. 2209248) and the 73 strain (VKPM B-8126, Russian Patent No. 2215782), which are resistant to norleucine, which is an analogue of L-methionine, and E. coli AJ13425 (FERM P-16808, Japanese Patent Laid-open (Kokai) No. 2000-139471). The AJ13425 strain is an L-threonine auxotrophic strain derived from the E. coli W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting or enhancing L-leucine-producing ability include, for example, a method of modifying a bacterium so that the bacterium has an increased activity or activities of one or more of the L-leucine biosynthesis enzymes. Examples of such enzymes include, but are not particularly limited to, the enzymes encoded by the genes of the leuABCD operon. Furthermore, for enhancing the activity of such an enzyme, for example, the mutant leuA gene encoding an isopropyl maleate synthase desensitized to feedback inhibition by L-leucine (U.S. Pat. No. 6,403,342) can be used.

Specific examples of L-leucine-producing bacteria and parental strains that can be used to derive them include, for example, strains belonging to the genus Escherichia, such as E. coli strains resistant to leucine (for example, the 57 strain (VKPM B-7386, U.S. Pat. No. 6,124,121)), E. coli strains resistant to a leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879), E. coli strains obtained by a gene engineering technique described in WO96/06926, and E. coli H-9068 (Japanese Patent Laid-open (Kokai) No. 8-70879).

<L-Isoleucine-Producing Bacteria>

Examples of methods for imparting or enhancing L-isoleucine-producing ability include, for example, a method of modifying a bacterium so that the bacterium has increased activity or activities of the L-isoleucine biosynthesis enzymes. Examples of such enzymes include, but are not particularly limited to, threonine deaminase and acetohydroxy acid synthase (Japanese Patent Laid-open (Kokai) No. 2-458, EP0356739A, U.S. Pat. No. 5,998,178).

Specific examples of L-isoleucine-producing bacteria and parental strains that can be used to derive them include, for example, Escherichia bacteria such as mutant strains having resistance to 6-dimethylaminopurine (Japanese Patent Laid-open (Kokai) No. 5-304969), mutant strains having resistance to an isoleucine analogue such as thiaisoleucine and isoleucine hydroxamate, and mutant strains having resistance to such an isoleucine analogue and further having resistance to DL-ethionine and/or arginine hydroxamate (Japanese Patent Laid-open (Kokai) No. 5-130882).

<L-Valine-Producing Bacteria>

Examples of methods for imparting or enhancing L-valine-producing ability include, for example, a method of modifying a bacterium so that the bacterium has an increased activity or activities of one or more of the L-valine biosynthesis enzymes. Examples of such enzymes include, but are not particularly limited to, the enzymes encoded by the ilvGMED genes of the ilvGMEDA operon and the enzymes encoded by the genes of the ilvBNC operon. The ilvGM genes encode an isozyme II of acetohydroxy acid synthase (AHAS II), the ilvE gene encodes transaminase, and the ilvD gene encodes dihydroxy acid dehydratase. The ilvBN genes encode an isozyme I of acetohydroxy acid synthase (AHAS I), and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, to enhance the activity of such an enzyme, the suppression of expression by the produced L-valine can be released by removing or modifying a region required for the attenuation. Furthermore, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, when using the ilvGMEDA operon for L-valine production, the operon can be used after disrupting or deleting the ilvA gene so that a functional threonine deaminase is not expressed.

Examples of methods for imparting or enhancing L-valine-producing ability also include, for example, a method of modifying a bacterium so that the bacterium has a reduced activity or activities of one or more of the enzymes that catalyze a reaction branching away from the biosynthesis pathway of L-valine to generate a compound other than L-valine. Examples of such enzymes include, but are not particularly limited to, threonine deaminase (ilvA) involved in the L-leucine synthesis, and enzymes involved in the D-pantothenic acid synthesis (panB, panC) (WO00/50624).

Specific examples of L-valine-producing bacteria and parental strains that can be used to derive them include, for example, E. coli strains modified so as to overexpress the ilvGMEDA operon (U.S. Pat. No. 5,998,178).

Examples of L-valine-producing bacteria and parental strains that can be used to derive them also include mutant strains having a mutation in amino-acyl t-RNA synthetase (U.S. Pat. No. 5,658,766). Examples of such strains include, for example, E. coli VL1970, which has a mutation in the ileS gene encoding isoleucine t-RNA synthetase. E. coli VL1970 was deposited at the Russian National Collection of Industrial Microorganisms (VKPM, FGUP GosNII Genetika, 1 Dorozhny Proezd, 1 Moscow 117545, Russia) on Jun. 24, 1988 under the accession number of VKPM B-4411. Examples of L-valine-producing bacteria and parental strains that can be used to derive them also include mutant strains requiring lipoic acid for growth and/or lacking H$^+$-ATPase (WO96/06926).

<L-Tryptophan-Producing Bacteria, L-Phenylalanine-Producing Bacteria, and L-Tyrosine-Producing Bacteria>

Examples of methods for imparting or enhancing L-tryptophan-producing ability, L-phenylalanine-producing ability, and/or L-tyrosine-producing ability include, for example, a method of modifying a bacterium so that the bacterium has an increased activity or activities of the L-tryptophan, L-phenylalanine, and/or L-tyrosine biosynthesis enzymes.

Examples of enzymes common to the biosynthesis systems of these aromatic amino acids include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP763127B). The expressions of the genes encoding these enzymes are controlled by the tyrosine repressor (tyrR), and the activities of these enzymes may be enhanced by deleting the tyrR gene (EP763127B).

Examples of the L-tryptophan biosynthesis enzymes include, but are not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase is made up of α and β subunits encoded by the trpA and trpB genes, respectively. Since the anthranilate synthase is subject to feedback inhibition by L-tryptophan, a gene encoding this enzyme introduced with a mutation for desensitization to feedback inhibition may be used for enhancing the activity of that enzyme. Since the phosphoglycerate dehydrogenase is subject to feedback inhibition by L-serine, a gene encoding this enzyme introduced with a mutation for desensitization to feedback inhibition may be used for enhancing the activity of that enzyme. Furthermore, by increasing the expression of the operon (ace operon) made up of the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthesis enzymes include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, genes encoding these enzymes introduced with a mutation for desensitization to feedback inhibition may be used for enhancing the activities of these enzymes.

Examples of the L-tyrosine biosynthesis enzymes include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, genes encoding these enzymes introduced with a mutation for desensitization to feedback inhibition may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Furthermore, the L-tryptophan, L-phenylalanine, and/or L-tyrosine-producing bacteria may be modified so that a by-product uptake system is enhanced. Examples of the by-product include aromatic amino acids other than the objective aromatic amino acid. Examples of the gene encoding such a by-product uptake system include, for example, tnaB and mtr, which are genes encoding the L-tryptophan uptake system, pheP, which is a gene encoding the L-phenylalanine uptake system, and tyrP, which is a gene encoding the L-tyrosine uptake system (EP1484410).

Specific examples of L-tryptophan-producing bacteria and parental strains that can be used to derive them include, for example, E. coli JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), E. coli SV164, which has a trpE allele encoding an anthranilate synthase desensitized to feedback inhibition by tryptophan, E. coli SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), E. coli AGX17(pGX44) (NRRL B-12263) and AGX6(pGX50)aroP (NRRL B-12264), which are deficient in tryptophanase (U.S. Pat. No. 4,371,614), E. coli AGX17/pGX50, pACKG4-pps, which has an increased phosphoenolpyruvate-producing ability (WO97/08333, U.S. Pat. No. 6,319,696), and strains belonging to the genus Escherichia having an increased activity of the protein encoded by the yedA or yddG gene (US2003-0148473A1 and US2003-0157667A1).

Specific examples of L-phenylalanine-producing bacteria and parental strains that can be used to derive them include, for example, E. coli AJ12739 (tyrA::Tn10, tyrR) (VKPM B-8197), which is deficient in the chorismate mutase-prephenate dehydrogenase and the tyrosine repressor (WO03/044191), E. coli HW1089 (ATCC 55371), which contains a mutant pheA34 gene encoding a chorismate mutase-prephenate dehydratase desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Specific examples of L-phenylalanine-producing bacteria and parental strains that can be used to derive them also include, for example, E. coli K-12<W3110(tyrA)/pPHAB> (FERM BP-3566), E. coli K-12<W3110(tyrA)/pPHAD> (FERM BP-12659), E. coli K-12 <W3110(tyrA)/pPHATerm> (FERM BP-12662), and E. coli K-12 AJ12604<W3110(tyrA)/pBR-aroG4, pACMAB> (FERM BP-3579), which contains a gene encoding a chorismate mutase-prephenate dehydratase desensitized to feedback inhibition (EP488424B1). Specific examples of L-phenylalanine-producing bacteria and parental strains that can be used to derive them further include, for example, strains belonging to the genus Escherichia having an increased activity of the protein encoded by the yedA gene or the yddG gene (US2003-0148473A, US2003-0157667A, WO03/044192).

Furthermore, examples of methods for imparting or enhancing an L-amino acid-producing ability include, for example, a method of modifying a bacterium so that the bacterium has an increased activity for secreting an L-amino acid from a bacterial cell. Such an activity for secreting an L-amino acid can be increased by, for example, increasing the expression of a gene encoding a protein responsible for secretion of the L-amino acid. Examples of genes encoding the proteins responsible for secretion of various amino acids include, for example, b2682 gene (ygaZ), b2683 gene (ygaH), b1242 gene (ychE), and b3434 gene (yhgN) (Japanese Patent Laid-open (Kokai) No. 2002-300874).

Furthermore, examples of methods for imparting or enhancing an L-amino acid-producing ability also include, for example, a method of modifying a bacterium so that the bacterium has an increased activity or activities of one or more proteins involved in the glycometabolism and proteins involved in the energy metabolism.

Examples of the proteins involved in the glycometabolism include proteins involved in uptake of saccharides and the glycolysis system enzymes. Examples of genes encoding a protein involved in the glycometabolism include glucose-6-phosphate isomerase gene (pgi, WO01/02542), pyruvate carboxylase gene (pyc, WO99/18228, EP1092776A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP1149911A), and sucrose assimilation gene (scrAB operon, U.S. Pat. No. 7,179,623).

Examples of genes encoding the proteins involved in the energy metabolism include the transhydrogenase gene (pntAB, U.S. Pat. No. 5,830,716) and cytochrome bo-type oxidase gene (cyoB, EP1070376A).

Furthermore, examples of methods for imparting or enhancing an ability to produce useful substances such as L-amino acids include, for example, a method of modifying a bacterium so that the activity of phosphoketolase is increased (WO2006/016705). Hence, the bacterium may be modified so that the activity of phosphoketolase is increased. This method may be effective particularly for imparting or enhancing an ability to produce an L-amino acid of glutamate family such as L-glutamic acid. Examples of phosphoketolase include D-xylulose-5-phosphate phosphoketolase and fructose-6-phosphate phosphoketolase. Either one of the D-xylulose-5-phosphate phosphoketolase activity and the fructose-6-phosphate phosphoketolase activity may be enhanced, or both may be enhanced.

The term "D-xylulose-5-phosphate phosphoketolase activity" refers to an activity for converting xylulose-5-phosphate into glycelaldehyde-3-phosphate and acetyl phosphate with consuming phosphoric acid to release one molecule of $H_2O$. This activity can be measured by the method described by Goldberg, M. et al. (Methods Enzymol., 9, 515-520, 1966) or the method described by L. Meile (J. Bacteriol., 183:2929-2936, 2001). Examples of D-xylulose-5-phosphate phosphoketolase include those of bacteria belonging to the genera *Acetobacter, Bifidobacterium, Lactobacillus, Thiobacillus, Streptococcus, Methylococcus, Butyrivibrio,* and *Fibrobacter*, and yeast belonging to the genera *Candida, Rhodotorula, Rhodosporidium, Pichia, Yarrowia, Hansenula, Kluyveromyces, Saccharomyces, Trichosporon,* and *Wingea*. Specific examples of D-xylulose-5-phosphate phosphoketolase and genes encoding them are disclosed in WO2006/016705.

The term "fructose-6-phosphate phosphoketolase activity" refers to an activity for converting fructose-6-phosphate into erythrose-4-phosphate and acetyl phosphate with consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001). Examples of fructose-6-phosphate phosphoketolase include those of bacteria belonging to the genera *Acetobacter, Bifidobacterium, Chlorobium, Brucella, Methylococcus,* and *Gardnerella*, and yeast belonging to the genera *Rhodotorula, Candida,* and *Saccharomyces*. Specific examples of fructose-6-phosphate phosphoketolase and genes encoding them are disclosed in WO2006/016705.

Both the D-xylulose-5-phosphate phosphoketolase activity and the fructose-6-phosphate phosphoketolase activity may also be retained by a single enzyme (i.e. D-xylulose-5-phosphate phosphoketolase/fructose-6-phosphate phosphoketolase).

The genes and proteins used for breeding L-amino acid-producing bacteria may have, for example, the nucleotide sequences and amino acid sequences of known genes and proteins, such as those exemplified above, respectively.

Also, the genes and proteins used for breeding L-amino acid-producing bacteria may be conservative variants of known genes and proteins, such as those exemplified above, respectively. Specifically, for example, the genes used for breeding L-amino acid-producing bacteria may each be a gene encoding a protein having an amino acid sequence of a known protein, but which include substitution, deletion, insertion, or addition of one or several amino acid residues at one or several positions, so long as the original function thereof is maintained. For the conservative variants of genes and proteins, the descriptions concerning conservative variants of the target genes and the target proteins mentioned later can be similarly applied.

<1-2> Specific Feature

The bacterium can be modified so as to have the specific feature. The bacterium can be obtained by modifying a bacterium having an L-amino acid-producing ability so as to have the specific feature. The bacterium can also be obtained by modifying a bacterium so as to have the specific feature, and then imparting or enhancing an L-amino acid-producing ability. The bacterium may also be a bacterium that has acquired an L-amino acid-producing ability by being modified so as to have the specific feature. The bacterium may have, as required, such a property possessed by an L-amino acid-producing bacterium as described above, as well as being modified so as to have the specific feature. The modifications for constructing the bacterium can be performed in any order.

By modifying a bacterium so as to have the specific feature, an L-amino acid-producing ability of the bacterium can be improved, that is, production of an L-amino acid by using the bacterium can be increased. Examples of the "increase in production of an L-amino acid" include an improvement, i.e. an increase, of the accumulation amount of an L-amino acid in a culture medium.

Examples of the specific feature include a modification of a c1795 gene. The modification of the c1795 gene is not particularly limited, so long as it improves the L-amino acid-producing ability. Examples of the modification of the c1795 gene include a modification of reducing the activity of a protein encoded by this gene (c1795 protein). That is, the bacterium may be modified so that the activity of the c1795 protein is reduced. The bacterium may be modified specifically so that the activity of the c1795 protein is reduced as compared with a non-modified strain. The phrase "the activity of a c1795 protein is reduced" may also mean that, particularly, the expression of the c1795 protein is reduced. The phrase "the activity of a c1795 protein is reduced" may also mean that, more particularly, the number of molecules of the c1795 protein per cell is reduced. Furthermore, the phrase "the activity of a c1795 protein is reduced" may also mean that, particularly, the function of each molecule of the c1795 protein is reduced. In other words, particular examples of the modification of the c1795 gene include a modification of reducing the number of molecules of the c1795 protein per cell and a modification of reducing the function of each molecule of the c1795 protein.

The c1795 protein is presumed to be a transcriptional regulator belonging to the Rrf2 family. The c1795 protein is involved in repression of the expression of several genes. A gene of which the expression is repressed by the c1795 protein is also referred to as an "expression-repressed gene". A protein encoded by an expression-repressed gene is also referred to as an "expression-repressed protein". Furthermore, for convenience of distinguishing proteins, an expression-repressed protein can also be referred to as a "protein P". The phrase "expression of a certain gene" and the phrase "expression of a protein encoded by a certain gene" may be used synonymously. That is, the phrase "expression-repressed protein" can refer to, in other words, a protein of which the expression is repressed by the c1795 protein.

Methods for reducing the activity of the c1795 protein are described below. The activity of the c1795 protein can be reduced by, for example, reducing the expression of the c1795 gene or disrupting the c1795 gene. Such methods for reducing the activity of the c1795 protein can be used independently or in any appropriate combination.

Examples of the specific feature also include a modification of increasing the activity of an expression-repressed protein. The phrase "the activity of an expression-repressed protein is increased" may also mean that, particularly, the expression of the expression-repressed protein is increased. The phrase "the activity of an expression-repressed protein is increased" may also mean that, more particularly, the number of molecules of the expression-repressed protein per cell is increased.

Examples of the expression-repressed protein include a protein encoded by a PAJ_1175 gene (PAJ_1175 protein), a protein encoded by a PAJ_1174 gene (PAJ_1174 protein), and a protein encoded by a PAJ_1173 gene (PAJ_1173 protein). The PAJ_1175 protein is presumed to be a transcriptional regulator belonging to the AraC family. The PAJ_1174 protein is presumed to be a periplasm adapter subunit of a multi-drug efflux transporter belonging to the RND (resistance-nodulation-cell division) superfamily. The PAJ_1173 protein is presumed to be a permease subunit of a multi-drug efflux transporter belonging to the RND (resistance-nodulation-cell division) superfamily. Regarding the expression-repressed protein, the activity of one expression-repressed protein may be increased, or the activities of two or more expression-repressed proteins may be increased. That is, for example, the activity of the PAJ_1175 protein, the activity of the PAJ_1174 protein, the activity of the PAJ_1173 protein, the activities of the PAJ_1175 protein and PAJ_1174 protein, the activities of the PAJ_1175 protein and PAJ_1173 protein, the activities of the PAJ_1174 protein and PAJ_1173 protein, or the activities of all of the PAJ_1175 protein, PAJ_1174 protein, and PAJ_1173 protein may be increased. Regarding the PAJ_1174 protein and PAJ_1173 protein, the activity or activities of either one or both of them may be increased. Regarding the PAJ_1174 protein and PAJ_1173 protein, typically, the activities of both of them may be increased. That is, for example, at least the activity of the PAJ_1175 protein may be increased, or at least the activities of the PAJ_1174 protein and PAJ_1173 protein may be increased.

Methods for increasing the activity of the expression-repressed protein are described below. The activity of the expression-repressed protein can be increased by, for example, increasing the expression of the expression-repressed gene. The expression of the expression-repressed gene can be increased by, for example, increasing the copy number of the expression-repressed gene or modifying an expression control sequence of the expression-repressed gene. In addition, the expression of the expression-repressed gene can be increased by, for example, reducing the activity of the c1795 protein. Such methods for increasing the activity of the expression-repressed protein can be used independently or in any appropriate combination.

The bacterium as described herein may have the feature(s) exemplified above independently or in any appropriate combination. That is, the bacterium may have, for example, one or both of the following features (A) and/or (B): (A) the bacterium has been modified so that the activity of a c1795 protein is reduced; (B) the bacterium has been modified so that the activity of a protein is increased, wherein the expression of the gene encoding the protein ("expression-repressed protein") is repressed by a c1795 protein.

The c1795 gene and the expression-repressed gene are also collectively referred to as "target genes". The c1795 protein and the expression-repressed protein are also collectively referred to as "target proteins".

Examples of the target genes and the target proteins include those of various organisms such as the bacteria belonging to the family Enterobacteriaceae exemplified above and other bacteria. The nucleotide sequences of target genes derived from various organisms and the amino acid sequences of target proteins encoded thereby can be obtained from, for example, public databases such as NCBI or technical documents such as patent documents. Incidentally, as the c1795 gene and the c1795 protein, it is sufficient that those native to or derived from a non-modified strain (specifically, a strain before being modified so that the activity of the c1795 protein is reduced) is selected. The phrase "a c1795 gene native to or derived from a non-modified strain" may refer to a c1795 gene present on the chromosome of the non-modified strain. The phrase "a c1795 protein native to or derived from a non-modified strain" may refer to a protein encoded by a c1795 gene present on the chromosome of the non-modified strain.

The c1795 gene of *P. ananatis* AJ13355 is located at positions 1401350 to 1401751 of the genome sequence of this strain (GenBank Accession Number AP012032.2). In this strain, the PAJ_1175 gene, PAJ_1174 gene, and PAJ_1173 gene are each located adjacent to the c1795 gene. The PAJ_1174 gene and PAJ_1173 gene may constitute an operon. The nucleotide sequence of the c1795 gene of *P. ananatis* AJ13355 and the amino acid sequence of the protein encoded by the gene are shown in SEQ ID NOS: 1 and 2, respectively. The nucleotide sequence of the PAJ_1175 gene of *P. ananatis* AJ13355 and the amino acid sequence of the protein encoded by the gene are shown in SEQ ID NOS: 3 and 4, respectively. The nucleotide sequence of the PAJ_1174 gene of *P. ananatis* AJ13355 and the amino acid sequence of the protein encoded by the gene are shown in SEQ ID NOS: 5 and 6, respectively. The nucleotide sequence of the PAJ_1173 gene of *P. ananatis* AJ13355 and the amino acid sequence of the protein encoded by the gene are shown in SEQ ID NOS: 7 and 8, respectively. That is, the target genes may each be, for example, a gene having the nucleotide sequence of any of the target genes exemplified above, such as the nucleotide sequence shown as SEQ ID NO: 1, 3, 5, or 7 respectively for the c1795 gene, PAJ_1175 gene, PAJ_1174 gene, or PAJ_1173 gene. Also, the target proteins may each be, for example, a protein having the amino acid sequence of any of the target proteins exemplified above, such as the amino acid sequence shown as SEQ ID NO: 2, 4, 6, or 8 respectively for the c1795 protein, PAJ_1175 protein, PAJ_1174 protein, or PAJ_1173 protein. The phrase "a gene or protein has a nucleotide or amino acid sequence" means that a gene or protein includes the nucleotide or amino acid sequence unless otherwise stated, and also includes cases where a gene or protein includes only the nucleotide or amino acid sequence.

The target genes may each be a variant of any of the target genes exemplified above (e.g. a gene having the nucleotide sequence shown as SEQ ID NO: 1, 3, 5, or 7 respectively for the c1795 gene, PAJ_1175 gene, PAJ_1174 gene, or PAJ_1173 gene, so long as the original function thereof is maintained. Similarly, the target proteins may each be a variant of any of the target proteins exemplified above (e.g. a protein having the amino acid sequence shown as SEQ ID NO: 2, 4, 6, or 8 respectively for the c1795 protein, PAJ_1175 protein, PAJ_1174 protein, or PAJ_1173 protein), so long as the original function thereof is maintained. Such a variant that maintains the original function thereof is also referred to as "conservative variant". The phrases "c1795 gene", "PAJ_1175 gene", "PAJ_1174 gene", and "PAJ_1173 gene" include not only the c1795 gene, PAJ_1175 gene, PAJ_1174 gene, and PAJ_1173 gene exemplified above, respectively, but also include conservative variants thereof. Similarly, the phrases "c1795 protein", "PAJ_1175 protein", "PAJ_1174 protein", and "PAJ_1173 protein" include not only the c1795 protein, PAJ_1175 protein, PAJ_1174 protein, and PAJ_1173 protein exemplified above, respectively, but also include conservative variants thereof. Examples of the conservative variants include, for example, homologues and artificially modified versions of the target genes and the target proteins exemplified above.

The phrase "the original function is maintained" means that a variant of a gene or protein has a function (such as activity or property) corresponding to the function (such as activity or property) of the original gene or protein. The phrase "the original function is maintained" used for a gene means that a variant of the gene encodes a protein that maintains the original function.

The phrase "the original function is maintained" used for the c1795 protein means that a variant of a protein has a function of a c1795 protein. The phrase "a function of a c1795 protein" may refer to a function of a protein having the amino acid sequence shown in SEQ ID NO: 2. The phrase "a function of a c1795 protein" may also refer to a function of a transcriptional regulator belonging to the Rrf2 family. The phrase "a function as a transcriptional regulator belonging to the Rrf2 family" may refer to, specifically, a function of repressing the expression of an expression-repressed gene such as the PAJ_1175 gene, PAJ_1174 gene, and PAJ_1173 gene. The phrase "a function of a c1795 protein" may also refer to a property that a reduced activity thereof in a bacterium belonging to the family Enterobacteriaceae improves an L-amino acid-producing ability of the bacterium.

The phrase "the original function is maintained" used for the PAJ_1175 protein means that a variant of a protein has a function as a PAJ_1175 protein. The phrase "a function as a PAJ_1175 protein" may refer to a function of a protein having the amino acid sequence shown in SEQ ID NO: 4. The phrase "a function as a PAJ_1175 protein" may also refer to a function as a transcriptional regulator belonging to the AraC family. The phrase "a function as a PAJ_1175 protein" may also refer to a property that an increased activity thereof in a bacterium belonging to the family Enterobacteriaceae improves an L-amino acid-producing ability of the bacterium.

The phrase "the original function is maintained" used for the PAJ_1174 protein means that a variant of a protein has a function of a PAJ_1174 protein. The phrase "a function as a PAJ_1174 protein" may refer to a function of a protein having the amino acid sequence shown in SEQ ID NO: 6. The phrase "a function as a PAJ_1174 protein" may also refer to a function of a periplasm adapter subunit of a multi-drug efflux transporter belonging to the RND (resistance-nodulation-cell division) superfamily. The phrase "a function of a periplasm adapter subunit of a multi-drug efflux transporter belonging to the RND superfamily" may refer to, specifically, a property of functioning as a multi-drug efflux transporter in combination with the PAJ_1173 protein. The phrase "a function of a PAJ_1174 protein" may also refer to a property that an increased activity thereof in a bacterium belonging to the family Enterobacteriaceae improves an L-amino acid-producing ability of the bacterium.

The phrase "the original function is maintained" used for the PAJ_1173 protein means that a variant of a protein has a function as a PAJ_1173 protein. The phrase "a function of a PAJ_1173 protein" may refer to a function of a protein having the amino acid sequence shown in SEQ ID NO: 8. The phrase "a function as a PAJ_1173 protein" may also refer to a function as a permease subunit of a multi-drug efflux transporter belonging to the RND (resistance-nodulation-cell division) superfamily. The phrase "a function of a permease subunit of a multi-drug efflux transporter belonging to the RND superfamily" may refer to, specifically, a property of functioning as a multi-drug efflux transporter in combination with the PAJ_1174 protein. The phrase "a function of a PAJ_1173 protein" may also refer to a property that an increased activity thereof in a bacterium belonging to the family Enterobacteriaceae improves an L-amino acid-producing ability of the bacterium.

Whether or not a variant of the c1795 protein has a function of a transcriptional regulator belonging to the Rrf2 family can be confirmed by, for example, confirming whether or not the expression of an expression-repressed gene such as the PAJ_1175 gene, PAJ_1174 gene, and PAJ_1173 gene is increased when reducing the activity of the variant in a bacterium belonging to the family Enterobacteriaceae. The function of other target proteins can also be confirmed by a method dependent on the type of the function.

Whether or not a variant of the target proteins has a property that a reduced or increased activity thereof in a bacterium belonging to the family Enterobacteriaceae improves an L-amino acid-producing ability of the bacterium can be confirmed by, for example, confirming whether or not an L-amino acid-producing ability is improved when reducing or increasing the activity of the variant in a bacterium belonging to the family Enterobacteriaceae.

Hereinafter, examples of the conservative variants will be explained.

Homologues of the target genes or homologues of the target proteins can be easily obtained from public databases by, for example, BLAST search or FASTA search using any of the nucleotide sequences of the target genes exemplified above or any of the amino acid sequences of the target proteins exemplified above as a query sequence. Furthermore, homologues of the target genes can be obtained by, for example, PCR using a chromosome of various organisms as the template, and oligonucleotides prepared on the basis of any of the nucleotide sequences of these known target genes as primers.

The target genes may each be a gene encoding a protein having any of the aforementioned amino acid sequences (e.g. the amino acid sequence shown as SEQ ID NO: 2, 4, 6, or 8 respectively for the c1795 protein, PAJ_1175 protein, PAJ_1174 protein, or PAJ_1173 protein), but which includes substitution, deletion, insertion, and/or addition of one or several amino acid residues at one or several positions, so long as the original function is maintained. For example, the N-terminus and/or the C-terminus of the encoded protein may be elongated or shortened. Although the number meant by the term "one or several" mentioned above may differ depending on the positions of amino acid residues in the three-dimensional structure of the protein or the types of amino acid residues, specifically, it can be, for example, 1 to 50, 1 to 40, or 1 to 30, 1 to 20, 1 to 10, 1 to 5, or 1 to 3.

The aforementioned substitution, deletion, insertion, and/or addition of one or several amino acid residues are/is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as described above includes a naturally occurring mutation due to an individual difference, or a difference of species of the organism from which the gene is derived (mutant or variant).

The target genes may each be a gene encoding a protein having an amino acid sequence having an identity of, for example, 50% or more, 65% or more, or 80% or more, 90% or more, 95% or more, 97% or more, or 99% or more, to the total amino acid sequence of any of the aforementioned amino acid sequences, so long as the original function is maintained.

The target genes may also each be a gene, such as DNA, that is able to hybridize under stringent conditions with a probe that can be prepared from any of the aforementioned nucleotide sequences (e.g. the nucleotide sequence shown as SEQ ID NO: 1, 3, 5, or 7 respectively for the c1795 gene, PAJ_1175 gene, PAJ_1174 gene, or PAJ_1173 gene), such as a sequence complementary to a partial or entire sequence of any of the aforementioned nucleotide sequences, so long as the original function is maintained. The term "stringent conditions" refers to conditions under which a so-called specific hybrid is formed, and a non-specific hybrid is not formed. Examples of the stringent conditions include those under which highly identical DNAs hybridize to each other, for example, DNAs not less than 50%, 65%, or 80% identical, not less than 90% identical, not less than 95% identical, not less than 97% identical, or not less than 99% identical, hybridize to each other, and DNAs less identical than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, any codons in the target genes may be replaced with respective equivalent codons. That is, the target genes may each be a variant of any of the target genes exemplified above due to the degeneracy of the genetic code. For example, the expression-repressed gene may be a gene modified so that it has optimal codons according to codon frequencies in the chosen host.

The term "identity" between amino acid sequences means an identity calculated by blastp with default scoring parameters (i.e. Matrix, BLOSUM62; Gap Costs, Existence=11, Extension=1; Compositional Adjustments, Conditional compositional score matrix adjustment). The term "identity" between nucleotide sequences means an identity calculated by blastn with default scoring parameters (i.e. Match/Mismatch Scores=1, −2; Gap Costs=Linear).

The aforementioned descriptions concerning conservative variants of the genes and proteins can be similarly applied to variants of any proteins such as L-amino acid biosynthesis system enzymes and genes encoding them.

<1-3> Methods for Increasing Activity of Protein

Hereinafter, the methods for increasing the activity of a protein such as the expression-repressed protein will be explained.

The expression "the activity of a protein is increased" means that the activity of the protein is increased as compared with a non-modified strain. Specifically, the expression "the activity of a protein is increased" means that the activity of the protein per cell is increased as compared with that of a non-modified strain. The term "non-modified strain" refers to a control strain that has not been modified so that the activity of an objective protein is increased. Examples of the non-modified strain include a wild-type strain and parent strain. Specific examples of the non-modified strain include the respective type strains of the species of bacteria. Specific examples of the non-modified strain also include strains exemplified above in relation to the description of bacteria. That is, in an embodiment, the activity of a protein may be increased as compared with a type strain, i.e. the type strain of the species to which the bacterium belongs. In another embodiment, the activity of a protein may also be increased as compared with the *E. coli* K-12 MG1655 strain. In another embodiment, the activity of a protein may also be increased as compared with the *P. ananatis* AJ13355 strain. In another embodiment, the activity of a protein may also be increased as compared with the *P. ananatis* NA1 strain. The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the gene (i.e. the amount of the protein). The term "the number of molecules of a protein per cell" may mean an average value of the number of molecules of the protein per cell. Furthermore, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" means that the expression of the gene is increased as compared with a non-modified strain such as a wild-type strain and parent strain. Specifically, the expression "the expression of a gene is increased" means that the expression amount of the gene per cell is increased as compared with that of a non-modified strain. The term "the expression amount of a gene per cell" may mean an average value of the expression amount of the gene per cell. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased to, for example, 1.5 times or more, 2 times or more, or 3 times or more of that of a non-modified strain. Furthermore, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a nucleotide sequence which is present in multiple copies on a chromosome as a target, multiple copies of a gene can be introduced into the chromosome. Examples of such a nucleotide sequence which is present in multiple copies on a chromosome include repetitive DNAs, and inverted repeats located at the both ends of a transposon. Alternatively, homologous recombination may be performed by using an appropriate nucleotide sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP805867B1). Such methods for modifying a chromosome using homologous recombination can be used for any modification on a chromosome, such as a modification of an expression control sequence, as well as for introduction of an objective gene.

Introduction of an objective gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of an objective gene can be increased by ligating a DNA fragment containing the objective gene with a vector that functions in a host to construct an expression vector of the gene, and transforming the host with the expression vector. The DNA fragment containing the objective gene can be obtained by, for example, PCR using the genomic DNA of a microorganism having the objective gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF 1010.

When a gene is introduced, it is sufficient that the gene is expressibly harbored by a host. Specifically, it is sufficient that the gene is harbored by a host so that it is expressed under control by a promoter that functions in the host. The promoter is not particularly limited so long as it functions in the host. The term "promoter that functions in a host" refers to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as described herein may also be used.

A terminator for termination of gene transcription may be located downstream of the gene. The terminator is not particularly limited so long as it functions in the host. The terminator may be a terminator derived from the host, or a heterogenous terminator. The terminator may be the native terminator of the gene to be introduced, or a terminator of another gene. Specific examples of the terminator include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by the host. For example, all the genes may be carried by a single expression vector or a chromosome. Furthermore, the genes may be separately carried by two or more expression vectors, or separately carried by a single or two or more expression vectors and a chromosome. An operon made up of two or more genes may also be introduced. The phrase "introducing two or more genes" can mean, for example, introducing respective genes encoding two or more kinds of proteins (such as enzymes), and/or introducing respective genes encoding two or more subunits constituting a single protein complex (such as enzyme complex).

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a gene can be modified to obtain a variant thereof. A gene can be modified by a known technique. For example, an objective mutation can be introduced into an objective site of DNA by the site-specific mutation method. That is, the coding region of a gene can be modified by the site-specific mutation method so that a specific site of the encoded protein include substitution, deletion, insertion, and/or addition of amino acid residues. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

Incidentally, when a protein functions as a complex made up of a plurality of subunits, some or all of the subunits may be modified, so long as the activity of the protein is eventually increased. That is, for example, when the activity of a protein is increased by increasing the expression of a gene, the expression of some or all of the genes that encode the subunits may be enhanced. It is usually preferable to enhance the expression of all of the genes encoding the subunits. Furthermore, the subunits that make up the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene. Examples of the expression control sequence include, for example, a promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" refers to a promoter providing an improved transcription of a gene compared with an inherent wild-type promoter of the gene. Examples of stronger promoters include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Furthermore, as the stronger promoter, a highly-active existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherent wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a synonymous codon more frequently used. That is, the gene to be introduced may be modified, for example, so as to contain optimal codons according to the frequencies of codons observed in the chosen host. Codons can be replaced by, for example, the site-specific mutation method. Alternatively, a gene fragment in which objective codons are replaced may be totally synthesized. Frequencies of codons in various organisms are disclosed in the "Codon Usage Database" (kazusa.or.jp/codon; Nakamura, Y et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in any appropriate combination.

Furthermore, the modification that increases the activity of a protein can also be attained by, for example, enhancing the specific activity of the protein. Enhancement of the specific activity also includes desensitization to feedback inhibition. That is, when a protein is subject to feedback inhibition by a metabolite, the activity of the protein can be increased by making the bacterium harbor a gene encoding a mutant protein that has been desensitized to the feedback inhibition. The term "desensitization to feedback inhibition" includes complete elimination of the feedback inhibition, and attenuation of the feedback inhibition, unless otherwise stated. Also, a state of "being desensitized to feedback inhibition", i.e. a state that feedback inhibition is eliminated or attenuated, may also be referred to as "tolerant to feedback inhibition". A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, and/or addition of one or several amino acid residues at one or several position of the protein. The mutation can be introduced by, for example, such a site-specific mutation method as described above. The mutation may also be introduced by, for example, a mutagenesis treatment. Examples of the mutagenesis treatment include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in any appropriate combination with such methods for enhancing gene expression as mentioned above.

The method for the transformation is not particularly limited, and conventionally known methods can be used such as, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, microarray, RNA-seq, and so forth (Sambrook, J., et al., Molecular Cloning A Laboratory Manual/Third Edition, Cold Spring Harbor Laboratory Press, Cold Spring Harbor (USA), 2001). The amount of mRNA (such as the number of molecules of the mRNA per cell) may be increased to, for example, 1.5 times or more, 2 times or more, or 3 times or more of that of a non-modified strain.

An increase in the amount of a protein can be confirmed by Western blotting using antibodies (Sambrook, J., et al., Molecular Cloning A Laboratory Manual/Third Edition, Cold Spring Harbor Laboratory Press, Cold Spring Harbor (USA), 2001). The amount of the protein (such as the number of molecules of the protein per cell) may be increased to, for example, 1.5 times or more, 2 times or more, or 3 times or more of that of a non-modified strain.

The aforementioned methods for increasing the activity of a protein can be used for enhancement of the activities of any proteins and enhancement of the expression of any genes.

<1-4> Method for Reducing Activity of Protein

Hereinafter, the methods for reducing the activity of a protein such as the c1795 protein will be explained.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" refers to a control strain that has not been modified so that the activity of an objective protein is reduced. Examples of the non-modified strain include a wild-type strain and parent strain. Specific examples of the non-modified strain include the respective type strains of the species of bacteria. Specific examples of the non-modified strain also include strains exemplified above in relation to the description of bacteria. That is, in an embodiment, the activity of a protein may be reduced as compared with a type strain, i.e. the type strain of the species to which the bacterium belongs. In another embodiment, the activity of a protein may also be reduced as compared with the *E. coli* K-12 MG1655 strain. In another embodiment, the activity of a protein may also be reduced as compared with the *P. ananatis* AJ13355 strain. In another embodiment, the activity of a protein may also be reduced as compared with the *P. ananatis* NA1 strain. The phrase "the activity of a protein is reduced" can mean that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the gene (i.e. the amount of the protein). The term "the number of molecules of a protein per cell" may mean an average value of the number of molecules of the protein per cell. The phrase "the number of molecules of the protein per cell is reduced" can mean that the protein does not exist at all. The phrase "the function of each molecule of the protein is reduced" can mean that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain such as a wild-type strain and parent strain. Specifically, the expression "the expression of a gene is reduced" means that the expression of the gene per cell is reduced as compared with that of a non-modified strain. The phrase "the expression amount of a gene per cell" may mean an average value of the expression amount of the gene per cell. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence can be modified. The transcription efficiency of a gene can be reduced by, for example, replacing the promoter of the gene on a chromosome with a weaker promoter. The term "weaker promoter" means a promoter providing an attenuated transcription of a gene compared with an inherent wild-type promoter of the gene. Examples of weaker promoters include, for example, inducible promoters. That is, an inducible promoter may function as a weaker promoter under a non-induced condition, such as in the absence of the corresponding inducer. Furthermore, a partial or entire region of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" refers to deletion of a partial or entire region of the coding region of the gene. Furthermore, the entire gene including sequences upstream and downstream from the coding region of the gene on a chromosome may be deleted. Sequences upstream and downstream from the coding region of a gene may contain, for example, an expression control sequence of the gene. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, the reading frames of the sequences upstream and downstream from the region to be deleted may not be the same. Inconsistency of reading frames may cause a frameshift downstream of the region to be deleted.

Disruption of a gene can also be attained by, for example, introducing an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. The reading frames of the sequences upstream and downstream from the insertion site may not be the same. Inconsistency of reading frames may cause a frameshift downstream of the insertion site. The other nucleotide sequence is not particularly limited so long as a sequence that reduces or eliminates the activity of the encoded protein is chosen, and examples thereof include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be similarly applied to the position and length of the region to be deleted in deletion of the amino acid sequence of a protein.

In the case of the c1795 protein, for example, 10 residues, 20 residues, 25 residues, 30 residues, 35 residues, 40 residues, or 44 residues of the C-terminus of the amino acid sequence thereof may be at least deleted. In the case of the c1795 protein, particularly, 44 residues of the C-terminus of the amino acid sequence thereof may be at least deleted. For example, in the case of the c1795 protein shown in SEQ ID NO: 2, the amino acid sequence of the positions 90 to 133 of SEQ ID NO: 2 corresponds to the "44 residues of the C-terminus". In addition, in the case of the c1795 protein, a region in the amino acid sequence of the c1795 protein, which region corresponds to the aforementioned C-terminal region of SEQ ID NO: 2, such as 44 residues of the C-terminus, may be at least deleted. The position of the "aforementioned C-terminal region of SEQ ID NO: 2" in any chosen c1795 protein can be determined by, for example, performing alignment between the amino acid sequence of the chosen c1795 protein and the amino acid sequence of SEQ ID NO: 2. The alignment can be performed by, for example, using known gene analysis software. Specific examples of such software include DNASIS produced by Hitachi Solutions, GENETYX produced by Genetyx, and so forth (Elizabeth C. Tyler et al., Computers and Biomedical Research, 24(1), 72-96, 1991; Barton G J et al., Journal of molecular biology, 198(2), 327-37. 1987).

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene include a gene of which a partial or the entire region of the coding region is deleted, gene including a missense mutation, gene including a nonsense mutation, gene including a frame shift mutation, and gene introduced with an insertion sequence such as a transposon or marker gene. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth. Such methods for modifying a chromosome using homologous recombination can be used for any modification on a chromosome, such as a modification of an expression control sequence, as well as for disruption of an objective gene.

The modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in any appropriate combination.

When a protein functions as a complex made up of a plurality of subunits, some or all of the subunits may be modified, so long as the activity of the protein is eventually reduced. That is, for example, some or all of the genes that encode the respective subunits may be disrupted or the like. Furthermore, when there is a plurality of isozymes of a protein, some or all of the activities of the isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, microarray, RNA-seq, and so forth (Sambrook, J., et al., Molecular Cloning A Laboratory Manual/Third Edition, Cold Spring Harbor Laboratory Press, Cold Spring Harbor (USA), 2001). The amount of mRNA (such as the number of molecules of the mRNA per cell) may be reduced to, for example, 50% or less, 20% or less, 10% or less, 5% or less, or 0% of that of a non-modified strain.

A reduction in the amount of a protein can be confirmed by Western blotting using antibodies (Sambrook, J., et al., Molecular Cloning A Laboratory Manual/Third Edition, Cold Spring Harbor Laboratory Press, Cold Spring Harbor (USA), 2001). The amount of the protein (such as the number of molecules of the protein per cell) may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein as mentioned above can be applied to reduction in the activities of any proteins and reduction in the expression of any genes.

<2> Method for Producing L-Amino Acid

The method as described herein is a method for producing an L-amino acid including the steps of culturing the bacterium as described herein in a medium to accumulate an L-amino acid in the medium and/or cells of the bacterium, and collecting the L-amino acid from the medium and/or cells of the bacterium. The L-amino acid is as described above. One kind of L-amino acid may be produced, or two or more kinds of L-amino acids may be produced.

The medium to be used is not particularly limited, so long as the bacterium can proliferate in it, and an objective L-amino acid can be produced. As the medium, for example, a medium typically chosen for culture of bacteria such as Enterobacteriaceae bacteria can be used. As the medium, for example, a medium containing carbon source, nitrogen source, phosphorus source, and sulfur source, as well as components selected from other various organic components and inorganic components as required can be used. Types and concentrations of the medium components can be appropriately determined according to various conditions such as the type of chosen bacterium.

Specific examples of the carbon source include, for example, saccharides such as glucose, fructose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, and aliphatic acids. As the carbon source, plant-derived materials can be used. Examples of the plant include, for example, corn, rice, wheat, soybean, sugarcane, beet, and cotton. Examples of the plant-derived materials include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the bacterium. As the carbon source, a single kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Furthermore, when an auxotrophic mutant that requires an amino acid or the like for growth thereof is used, it is preferable to supply a required nutrient to the medium.

Furthermore, for example, the amount of biotin in the medium can be restricted, or a surfactant or penicillin can be added to the medium.

The culture conditions are not particularly limited so long as the bacterium can proliferate, and an objective L-amino acid can be produced. The culture can be performed, for example, under usual conditions used for culturing bacteria such as Enterobacteriaceae bacteria. The culture conditions can be appropriately set according to various conditions such as the type of bacterium to be used.

The culture can be performed by using a liquid medium. At the time of the culture, the bacterium cultured on a solid medium such as agar medium may be directly inoculated into a liquid medium, or the bacterium cultured in a liquid medium as seed culture may be inoculated into a liquid medium for main culture. That is, the culture may be performed separately as seed culture and main culture. In such a case, the culture conditions of the seed culture and the main culture may be or may not be the same. The amount of the bacterium present in the medium at the time of the start of the culture is not particularly limited. The main culture may be performed by, for example, inoculating a seed culture broth to a medium for main culture at an amount of 1 to 50% (v/v).

The culture can be performed as batch culture, fed-batch culture, continuous culture, or a combination of these. The medium used at the time of the start of the culture is also referred to as "starting medium". The medium supplied to a culture system (fermentation tank) in fed-batch culture or continuous culture is also referred to as "feed medium". Furthermore, to supply a feed medium to a culture system in fed-batch culture or continuous culture is also referred to as to "feed". Furthermore, when the culture is performed separately as seed culture and main culture, for example, both the seed culture and the main culture may be performed as batch culture. Alternatively, for example, the seed culture may be performed as batch culture, and the main culture may be performed as fed-batch culture or continuous culture.

The medium components each may be present in the starting medium, feed medium, or the both. The types of the components present in the starting medium may be or may not be the same as the types of the components present in the feed medium. The concentration of each component present in the starting medium may be or may not be the same as the concentration of the component present in the feed medium. Furthermore, two or more kinds of feed media containing different types and/or different concentrations of components may be used. For example, when medium is intermittently fed a plurality of times, the types and/or concentrations of components present in the feed media may be or may not be the same for each feeding.

The concentration of the carbon source in the medium is not particularly limited, so long as the bacterium can proliferate and produce an L-amino acid. The concentration of the carbon source in the medium may be as high as possible within such a range that production of the L-amino acid is not inhibited. The concentration of the carbon source in the medium may be, as the initial concentration (the concentration in the starting medium), for example, 1 to 30% (w/v), or 3 to 10% (w/v). Furthermore, the carbon source may be additionally supplied to the medium as required. For example, the carbon source may be additionally supplied to the medium in proportion to the consumption of the carbon source as the fermentation progresses.

The culture can be performed, for example, under an aerobic condition. The term "aerobic condition" refers to a condition where the dissolved oxygen concentration in the liquid medium is not lower than 0.33 ppm, which is the detection limit for the detection with an oxygen membrane electrode, or may be a condition where the dissolved oxygen concentration in the liquid medium is not lower than 1.5 ppm. The oxygen concentration can be controlled to, for example, 5 to 50%, or about 10%, of the saturated oxygen concentration. Specifically, the culture under an aerobic condition can be performed by aeration culture, shaking culture, stirring culture, or a combination thereof. The pH of the medium may be, for example, 3 to 10, or 4.0 to 9.5. During the culture, the pH of the medium can be adjusted as required. The pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, potassium hydroxide, calcium hydroxide, and magnesium hydroxide. The culture temperature may be, for example, 20 to 40° C., or 25 to 37° C. The culture period may be, for example, 10 to 120 hours. The culture may be continued, for example, until the carbon source contained in the medium is consumed, or until the bacterium loses the activity. By culturing the bacterium under such conditions as described above, an L-amino acid is accumulated in the medium and/or cells of the bacterium.

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated include, for example, pH 5.0 to 4.0, pH 4.5 to 4.0, pH 4.3 to 4.0, or around pH 4.0 (EP1078989A). When using a liquid medium adjusted to satisfy a condition under which L-glutamic acid is precipitated, L-glutamic acid can be more efficiently crystallized by adding pantothenic acid into the medium (WO2004/111258). Also, when using a liquid medium adjusted to satisfy a condition under which L-glutamic acid is precipitated, L-glutamic acid can be more efficiently crystallized by adding L-glutamic acid crystals as seed crystals into the medium (EP1233069A). Also, when using a liquid medium adjusted to satisfy a condition under which L-glutamic acid is precipitated, L-glutamic acid can be more efficiently crystallized by adding L-glutamic acid crystals and L-lysine crystals as seed crystals into the medium (EP1624069A).

For producing a basic amino acid such as L-lysine, the culture step (fermentation step) may be carried out so that bicarbonate ions and/or carbonate ions serve as counter ions for the basic amino acid. Such a fermentation mode is also referred to as "carbonate fermentation". By the carbonate fermentation, a basic amino acid can be produced by fermentation while reducing the amounts of sulfate ions and/or chloride ions to be used, which have been conventionally used as counter ions for a basic amino acid. The carbonate fermentation can be carried out, for example, as described in US2002-025564A, EP1813677A, and JP2002-65287A.

The fermentation broth can be processed by using, for example, a hydrocyclone. As the hydrocyclone, for example, one having an ordinary shape, having a cylindrical part having a diameter of 10 to 110 mm, and made of ceramic, stainless steel, or resin can be used. The feeding amount of the fermentation broth to the hydrocyclone can be set depending on, for example, the cell concentration and the L-amino acid concentration in the fermentation broth. The feeding amount of the fermentation broth to the hydrocyclone may be, for example, 2 to 1200 L/min.

Production of an L-amino acid can be confirmed by known methods used for detection or identification of compounds. Examples of such methods include, for example, HPLC, LC/MS, GC/MS, and NMR. These methods can be independently used, or can be used in an appropriate combination.

The produced L-amino acid can be collected from the fermentation broth by known methods used for separation and purification of compounds. Examples of such methods include, for example, ion-exchange resin method (Nagai, H. et al., Separation Science and Technology, 39(16), 3691-3710), precipitation, membrane separation (Japanese Patent Laid-open (Kokai) No. 9-164323 and Japanese Patent Laid-open (Kokai) No. 9-173792), and crystallization (WO2008/078448 and WO2008/078646). These methods can be independently used, or can be used in an appropriate combination. When the L-amino acid is accumulated in cells of the bacterium, for example, the cells can be disrupted with ultrasonic waves or the like, a supernatant can be obtained by removing the cells from the cell-disrupted suspension by centrifugation, and the L-amino acid can be collected from the supernatant by the ion exchange resin method or the like. The L-amino acid to be collected may be a free compound, a salt thereof, or a mixture thereof. Examples of the salt include, for example, sulfate, hydrochloride, carbonate, ammonium salt, sodium salt, and potassium salt. When L-glutamic acid is produced, L-glutamic acid to be collected may specifically be, for example, free L-glutamic acid, sodium L-glutamate (such as monosodium L-glutamate, MSG), ammonium L-glutamate (such as monoammonium L-glutamate), or a mixture of these. For example, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5). The monosodium L-glutamate crystal can be used as, for example, an umami seasoning. The monosodium L-glutamate crystal may also be used as a seasoning in combination with a nucleic acid such as sodium guanylate and sodium inosinate, which also have umami taste.

When the L-amino acid is precipitated in the medium, it can be collected by centrifugation, filtration, or the like. The L-amino acid precipitated in the medium may also be isolated together with the L-amino acid dissolving in the medium, after the L-amino acid dissolving in the medium is crystallized.

The collected L-amino acid may contain such components as bacterial cells, medium components, moisture, and by-product metabolites of the bacterium in addition to the L-amino acid. The collected L-amino acid may also be purified at a desired extent. The purity of the collected L-amino acid may be, for example, 50% (w/w) or higher, 85% (w/w) or higher, or 95% (w/w) or higher (JP1214636B, U.S. Pat. Nos. 5,431,933, 4,956,471, 4,777,051, 4,946,654, 5,840,358, 6,238,714, and US2005/0025878).

EXAMPLES

Hereinafter, the present invention will be more specifically explained with reference to the following non-limiting examples.

Example 1. L-Glutamic Acid Production Using *Pantoea ananatis* Strain Introduced with c1795 Nonsense Mutation In this Example, the effect of introduction of a nonsense mutation into the c1795 gene on L-glutamic acid production was evaluated. The c1795 gene is a novel gene found at positions 1401350 to 1401751 of the genome sequence of *Pantoea ananatis* AJ13355 (GenBank Accession Number AP012032.2).

(1) Construction of Strain Introduced with c1795 Nonsense Mutation

Construction of plasmid pUC18-c1795-($\lambda$attL-Km$^r$-$\lambda$attR)

A plasmid pUC18-c1795-($\lambda$attL-Km$^r$-$\lambda$attR), which contains the c1795 gene, was prepared. The plasmid pUC18-c1795-($\lambda$attL-Km$^r$-$\lambda$attR) can be constructed by the following procedures.

PCR is carried out by using chromosomal DNA of *Pantoea ananatis* AJ13355 (FERM BP-6614) as the template, and primers of SEQ ID NOS: 9 and 10, to amplify the c1795 gene. PCR is carried out by using a plasmid pMW118-($\lambda$attL-Km$^r$-$\lambda$attR) (WO2008/090770) as the template, and primers of SEQ ID NOS: 11 and 12, to amplify a $\lambda$attL-Km$^r$-$\lambda$attR region. A plasmid pUC18 is digested with restriction enzymes EcoRI and SalI. These three fragments are mutually ligated by using In-Fusion HD Cloning Kit (Clontech), to obtain a plasmid pUC18-c1795-($\lambda$attL-Km$^r$-$\lambda$attR), in which $\lambda$attL-Km$^r$-$\lambda$attR is ligated downstream of the c1795 gene.

(1-2) Construction of Plasmid pUC18-c1795mt-($\lambda$attL-Km$^r$-$\lambda$attR)

A plasmid pUC18-c1795mt-($\lambda$attL-Km$^r$-$\lambda$attR), which contains a mutant c1795 gene in which A (adenine) at position 268 was replaced with G (guanine) and C (cytosine) was inserted between the positions 266 and 267, was prepared. Incidentally, A of the stat codon ATG in the c1795 gene is regarded as position 1. In this mutant c1795 gene, a stop codon is located at positions 268 to 270. That is, this mutant c1795 gene encodes a mutant c1795 protein in which 44 residues of the C-terminus of the wild-type c1795 protein shown in SEQ ID NO: 2 (i.e. the amino acid sequence of the positions 90 to 133 of SEQ ID NO: 2) was deleted. The plasmid pUC18-c1795mt-($\lambda$attL-Km$^r$-$\lambda$attR) can be constructed by the following procedures.

First, PCR is carried out by using the plasmid pUC18-c1795-($\lambda$attL-Km$^r$-$\lambda$attR) as the template, and primers of SEQ ID NOS: 13 and 14, to amplify the full-length of this plasmid. Then, after digestion of the obtained PCR product with DpnI, *E. coli* JM109 is transformed with the digested product, applied to LB agar medium (Bacto tryptone 10 g/L, Yeast extract 5 g/L, NaCl 5 g/L, Agar 15 g/L, pH7.0) containing 25 µg/mL of kanamycin (Km), and cultured overnight at 37° C. Plasmids are extracted from colonies of grown transformants by a known method. The nucleotide sequences of the plasmids are determined by using a 3100 genetic analyzer (Applied Biosystems), and one confirmed to be introduced with the objective mutation is designated as pUC18-c1795mt-($\lambda$attL-Km$^r$-$\lambda$attR).

(1-3) Construction of Strain Introduced with c1795 Nonsense Mutation

PCR was carried out by using the plasmid pUC18-c1795mt-($\lambda$attL-Km$^r$-$\lambda$attR)) as the template, and primers of SEQ ID NOS: 15 and 16, to amplify a c1795mt-($\lambda$attL-Km$^r$-$\lambda$attR) fragment for Red recombination. The primer of SEQ ID NO: 15 contains a homologous sequence of the c1795 gene of *Pantoea ananatis* including a start codon. The primer of SEQ ID NO: 16 contains a homologous sequence of a downstream region of the c1795 gene of *Pantoea ananatis* and further contains a homologous sequence of 5' terminus of $\lambda$attL-Km$^r$-$\lambda$attR.

A helper plasmid RSF-Red-TER (WO2008/090770) was used as a carrier of Red genes of $\lambda$ phage. *Pantoea ananatis* SC17(0) (VKPM B-9246) transformed with the helper plasmid RSF-Red-TER was cultured overnight at 34° C. in LB medium (Bacto tryptone 10 g/L, Yeast extract 5 g/L, NaCl 5 g/L, pH7.0) containing 100 µg/mL of spectinomycin. Then, the culture broth was 100-fold diluted with a fresh LB medium containing 100 µg/mL of spectinomycin and 1 mM of IPTG, and cultured with shaking for 2.5 hours at 34° C. Cells were collected from 35 mL of the culture broth by centrifugation, washed three times with 25 mL, 10 mL, and 10 mL of 10% glycerol, and suspended in 300 µL of 10% glycerol, to obtain a suspension of competent cells. Immediately before electroporation, 600 ng of the c1795mt-($\lambda$attL-Km$^r$-$\lambda$attR) fragment dissolved in 2 µL of deionized water was added to 50 µL of the cell suspension. Electroporation was carried out by using a bacterial electroporation apparatus (BioRad, USA, catalog No. 165-2089, version 2-89). The pulse parameters used were as follows: electric field intensity, 17.5 kV/cm; and pulse time, 5 msec.

After the electroporation, 1 mL of SOC medium was immediately added to the cell suspension. Then, cells were cultured with aeration for 2 hours at 34° C., and further cultured on LB agar medium containing 40 µg/mL of kanamycin overnight at 34° C. The chromosomal structures of obtained kanamycin-resistant strains were confirmed by nucleotide sequencing analysis, and one confirmed to be introduced with the objective mutation into the c1795 gene on the chromosome was designated as SC17(0)::c1795mt.

Chromosomal DNA was extracted from the strain SC17 (0)::c1795mt by using PurElute Bacterial Genomic kit (EdgeBio). *Pantoea ananatis* NA1 (WO2008/090770) was introduced with the obtained chromosomal DNA by electroporation, and cultured on LB agar medium containing 40 µg/mL of kanamycin (Km) and 12.5 mg/L of tetracycline (Tet), to obtain approximately 20 colonies of transformants. The chromosomal structures of the obtained transformants were confirmed by nucleotide sequencing analysis, and one confirmed to be introduced with the objective mutation into the c1795 gene on the chromosome was designated as NA1-c1795mt.

(2) Evaluation of L-Glutamic Acid-Producing Ability of Strain Introduced with c1795 Nonsense Mutation For evaluating an effect of introduction of a nonsense mutation into the c1795 gene on L-glutamic acid production, test tube culture was carried out using the strain introduced with c1795 nonsense mutation (NA1-c1795mt) and the control strain (NA1) by the following procedures.

The strains NA1 and NA1-c1795mt were each applied to LB agar medium containing 12.5 mg/L of Tet, and cultured overnight at 34° C. Cells in an amount of half of a well-grown plate (approximately 5 µL) were inoculated into 5 mL of a test tube culture medium shown in Table 1 contained in a large test tube, and cultured for 19 hours at 34° C. on a reciprocal shaker (120 rpm). The OD620 value of the culture broth and the L-glutamic acid concentration in the culture supernatant at the completion of culture are shown in Table 2. A higher L-glutamic acid-producing ability was observed for the strain introduced with c1795 nonsense mutation (NA1-c1795mt) than the control strain (NA1).

TABLE 1

| Composition of test tube culture medium | |
|---|---|
| Component | Final concentration |
| Group A | |
| Ammonium sulfate | 20 g/L |
| KH$_2$PO$_4$ | 2 g/L |
| Yeast extract | 2 g/L |
| Lys | 0.2 g/L |
| Met | 0.2 g/L |
| DAP | 0.2 g/L |
| FeSO$_4$•7H$_2$O (10 g/L) | 20 mg/L |
| MnSO$_4$•7H$_2$O (10 g/L) | 20 mg/L |
| This group was adjusted to pH 7.0 with KOH and sterilized by autoclaving at 115° C. for 10 minutes. | |
| Group B | |
| Sucrose | 30 g/L |
| MgSO$_4$ •7H$_2$O | 0.5 g/L |
| This group was sterilized by autoclaving at 115° C. for 10 minutes. | |
| Group C | |
| Calcium carbonate (Kanto Chemical) | 20 g/L |
| This group was sterilized by dry heat sterilization at 180° C. for 3 hours or longer. | |

TABLE 2

| OD and production amount of L-glutamic acid in test tube culture of *Pantoea ananatis* strain introduced with c1795 nonsense mutation | | |
|---|---|---|
| Strain | OD620 | L-glutamic acid (g/L) |
| NA1 | 14.5 ± 0.08 | 12.6 ± 0.36 |
| NA1-c1795mt | 15.3 ± 0.57 | 15.0 ± 0.38 |

Example 2. L-Glutamic Acid Production Using *Pantoea ananatis* PAJ_1175 Gene-Amplified Strain and PAJ_1174-73 Gene-Amplified Strain It has been separately found that the expression of the PAJ_1175 gene, PAJ_1174 gene, and PAJ_1173 gene each located adjacent to the c1795 gene are each enhanced by introduction of a nonsense mutation into the c1795 gene (Data not shown). Thus, in this Example, an effect of enhancing expression of PAJ_1175 gene or PAJ_1174-73 gene on L-glutamic acid production was evaluated. The term "PAJ_1174-73 gene" refers to the PAJ_1174 gene and PAJ_1173 gene. The PAJ_1174-73 gene is considered to constitute an operon in *Pantoea ananatis* AJ13355 (FERM BP-6614).

(1) Construction of Plasmid for Amplifying PAJ_1175 Gene

As an expression vector, a plasmid pMIV-Pnlp8 (JP2010-187552A), which was constructed from a plasmid pMIV-5JS (JP2008-99668A), was used. As a control, the plasmid pMIV-5JS, which is a blank vector, was used. The plasmid pMIV-Pnlp8 has a potent promoter Pnlp8 and a rrnB terminator, and SalI and XbaI sites are located between the Pnlp8 and the rrnB terminator. Hence, when an objective gene is designed to contain a restriction enzyme site SalI or XhoI at 5'-side of the gene and a restriction enzyme site XbaI at 3'-side of the gene, the objective gene can be cloned between the Pnlp8 and the rrnB terminator, to construct an expression plasmid of the objective gene. The PAJ_1175 gene was amplified by PCR using chromosomal DNA of *Pantoea ananatis* AJ13355 (FERM BP-6614) as the template, and primers of SEQ ID NOS: 17 and 18. PCR was carried out by using KOD plus (TOYOBO) under the following conditions: 94° C. for 2 minutes, 30 cycles of (94° C. for 15 seconds, 45° C. for 30 seconds, and 68° C. for 1 minute/kb), and 68° C. for 10 minutes. The PCR product was digested with restriction enzymes SalI and XbaI, and ligated with the plasmid pMIV-Pnlp8 digested with restriction enzymes SalI and XbaI. *E. coli* JM109 was transformed with the ligation product, and clones each having a predicted sequence length of the PAJ_1175 gene. Plasmids were extracted from these clones by a conventional manner, and the nucleotide sequences of the plasmids were determined. A plasmid confirmed to be inserted with the PAJ_1175 gene was designated as pMIV-Pnlp8_PAJ_1175. The nucleotide sequence of pMIV-Pnlp8 PAJ_1175 is shown as SEQ ID NO: 19.

(2) Construction of Plasmid for Amplifying PAJ_1174-73 Gene

The PAJ_1174-73 gene was amplified by PCR using chromosomal DNA of *Pantoea ananatis* AJ13355 (FERM BP-6614) as the template, and primers of SEQ ID NOS: 20 and 21. PCR was carried out by using KOD plus (TOYOBO) under the following conditions: 94° C. for 2 minutes, 30 cycles of (94° C. for 15 seconds, 45° C. for 30 seconds, and 68° C. for 1 minute/kb), and 68° C. for 10 minutes. The PCR product was digested with restriction enzymes XhoI and XbaI, and ligated with the plasmid pMIV-Pnlp8 digested with restriction enzymes SalI and XbaI. *E. coli* JM109 was transformed with the ligation product, and clones each having a predicted sequence length of the PAJ_1174-73 gene. Plasmids were extracted from these clones by a conventional manner, and the nucleotide sequences of the plasmids were determined. A plasmid confirmed to be inserted with the PAJ_1174-73 gene was designated as pMIV-Pnlp8_PAJ_1174-73. The nucleotide sequence of pMIV-Pnlp8_PAJ_1174-73 is shown as SEQ ID NO: 22.

(3) Construction of PAJ_1175 Gene-Amplified Strain and PAJ_1174-73 Gene-Amplified Strain

*Pantoea ananatis* NA1 (WO2008/090770) was introduced with each of the plasmids pMIV-5JS, pMIV-Pnlp8_PAJ_1175, and pMIV-Pnlp8_PAJ_1174-73, and cultured on LB agar medium containing 20 mg/L of chloramphenicol at 34° C. for 18 hours, to obtain transformants. Strains introduced with the plasmids pMIV-5JS, pMIV-Pnlp8_PAJ_1175, and pMIV-Pnlp8_PAJ_1174-73 were designated as NA1/pMIV-5JS, NA1/pMIV-Pnlp8_PAJ_1175, and NA1/pMIV-5JS-Pnlp8 PAJ_1174-73, respectively.

(4) Evaluation of L-Glutamic Acid-Producing Ability of PAJ_1175 Gene-Amplified Strain and PAJ_1174-73 Gene-Amplified Strain Test tube culture was carried out using the control strain (NA1/pMIV-5JS), the PAJ_1175 gene-amplified strain (NA1/pMIV-Pnlp8 PAJ_1175), and the PAJ_1174-73 gene-amplified strain (NA1/pMIV-5JS-Pnlp8_PAJ_1174-73) in the same manner as Example 1(2). The OD620 value of the culture broth and the L-glutamic acid concentration in the culture supernatant at the completion of culture are shown in Table 3. A higher L-glutamic acid-producing ability was observed for each of the PAJ_1175 gene-amplified strain and PAJ_1174-73 gene-amplified strain than the control strain (NA1/pMIV-5JS).

TABLE 3

OD and production amount of L-glutamic acid in test tube culture of *Pantoea ananatis* PAJ_1175 gene-amplified strain and PAJ_1174-73 gene-amplified strain

| Strain | OD620 | L-glutamic acid (g/L) |
|---|---|---|
| NA1/pMIV-5JS | 20.4 ± 1.37 | 16.0 ± 0.92 |
| NA1/pMIV-Pnlp8_PAJ_1175 | 18.4 ± 0.26 | 18.4 ± 0.21 |
| NA1/pMIV-Pnlp8_PAJ_1174-73 | 19.9 ± 0.28 | 17.5 ± 0.17 |

Example 3. L-Glutamic Acid Production Using *Pantoea ananatis* c1795 Gene-Deletion Strain In this Example, an effect of deletion of the c1795 gene on L-glutamic acid production was evaluated.

(1) Construction of c1795 Gene-Deletion Strain

PCR was carried out by using the plasmid pMW118-(λattL-Km$^r$-λattR) as the template, and primers of SEQ ID NOS: 23 and 24, to amplify a DNA fragment of approximately 1.5 kbp for Red recombination. The primer of SEQ ID NO: 23 contains a homologous sequence of an upstream region of the c1795 gene of *Pantoea ananatis* and further contains a homologous sequence of 5' terminus of λattL-Km$^r$-λattR. The primer of SEQ ID NO: 24 contains a homologous sequence of a downstream region of the c1795 gene of *Pantoea ananatis* and further contains a homologous sequence of 3' terminus of λattL-Km$^r$-λattR. The amplified DNA fragment has a structure in which the homologous sequence of an upstream region of the c1795 gene, λattL-Km$^r$-λattR, and the downstream region of the c1795 gene were ligated in this order.

The DNA fragment was purified and then used for Red recombination. The helper plasmid RSF-Red-TER was used as a carrier of Red genes of λ phage. *Pantoea ananatis* SC17(0) (VKPM B-9246) transformed with the helper plasmid RSF-Red-TER was cultured overnight at 34° C. in LB medium containing 50 µg/mL of chloramphenicol. Then, the culture broth was 100-fold diluted with a fresh LB medium containing 50 µg/mL of chloramphenicol, and cultured with aeration at 34° C. until OD600 reached 0.3. Then, IPTG was added at a concentration of 1 mM, and culture was continued until OD600 reached 0.7. Cells were collected from 10 mL of the culture broth by centrifugation, washed three times with an equal volume of 10% cold glycerol, and suspended in 80 µL of 10% cold glycerol, to obtain a suspension of competent cells. The DNA fragment was dissolved in 10 µL of deionized water, and 100 to 200 ng of the DNA fragment was added to the cell suspension. Electroporation was carried out by using a bacterial electroporation apparatus (Bio-Rad, USA, catalog No. 165-2089, version 2-89). The pulse parameters used were as follows: electric field intensity, 18 kV/cm; and pulse time, 5 msec.

After the electroporation, 1 mL of LB medium supplemented with 0.5% of glucose was immediately added to the cell suspension. Then, cells were cultured with aeration for 2 hours at 34° C., and further cultured on LB agar medium containing 40 mg/L of kanamycin, to obtain approximately 20 colonies of transformants. PCR was performed by using primers of SEQ ID NOS: 25 and 26 to confirm that the c1795 gene region was replaced with λattL-Km$^r$-λattR, and a strain in which the replacement was confirmed was designated as SC17(0)::Δc1795.

Chromosomal DNA was extracted from the strain SC17(0)::Δc1795. *Pantoea ananatis* NA1 (WO2008/090770) was introduced with the obtained chromosomal DNA by electroporation, and cultured on LBGM9 agar medium containing 40 µg/mL of kanamycin and 12.5 mg/L of tetracycline hydrochloride, to obtain approximately 20 colonies of transformants. LBGM9 agar medium corresponds to LB agar medium added with minimal medium components (glucose 5 g/L, magnesium sulfate 2 mM, monopotassium phosphate 3 g/L, sodium chloride 0.5 g/L, ammonium chloride 1 g/L, and disodium phosphate 6 g/L). It was confirmed that the c1795 gene region was replaced with λattL-Km$^r$-λattR in each of these transformants. One clone of these transformants was designated as NA1::Δc1795.

(2) Evaluation of L-Glutamic Acid-Producing Ability of c1795 Gene-Deletion Strain Test tube culture was carried out using the control strain (NA1) and the c1795 gene-deletion strain (NA1::Δc1795) in the same manner as Example 1(2). The OD620 value of the culture broth and the L-glutamic acid concentration in the culture supernatant at the completion of culture are shown in Table 4. A higher L-glutamic acid-producing ability was observed for the c1795 gene-deletion strain than the control strain (NA1).

TABLE 4

OD and production amount of L-glutamic acid in test tube culture of *Pantoea ananatis* c1795 gene-deletion strain

| Strain | OD620 | L-glutamic acid (g/L) |
|---|---|---|
| NA1 | 12.4 ± 0.45 | 10.9 ± 0 |
| NA1::Δc1795 | 10.9 ± 0.8 | 11.65 ± 0.05 |

<Explanation of Sequence Listing>
SEQ ID NOS:
1: Nucleotide sequence of c1795 gene of *P. ananatis* AJ13355
2: Amino acid sequence of c1795 protein of *P. ananatis* AJ13355
3: Nucleotide sequence of PAJ_1175 gene of *P. ananatis* AJ13355
4: Amino acid sequence of PAJ_1175 protein of *P. ananatis* AJ13355
5: Nucleotide sequence of PAJ_1174 gene of *P. ananatis* AJ13355
6: Amino acid sequence of PAJ_1174 protein of *P. ananatis* AJ13355
7: Nucleotide sequence of PAJ_1173 gene of *P. ananatis* AJ13355
8: Amino acid sequence of PAJ_1173 protein of *P. ananatis* AJ13355
9-18: Primers
19: Nucleotide sequence of pMIV-Pnlp8 PAJ_1175
20-21: Primers
22: Nucleotide sequence of pMIV-Pnlp8 PAJ_1174-73
23-26: Primers

The invention claimed is:

1. A bacterium belonging to the family Enterobacteriaceae and having an L-amino acid-producing ability,
wherein the bacterium has a feature selected from the group consisting of:
(A) the bacterium has been modified so that the activity of a c1795 protein is reduced; and
(B) the bacterium has been modified so that the activity of a protein P is increased, wherein the expression of protein P is repressed by a c1795 protein;
wherein the c1795 protein and the protein P are native to a bacterium belonging to the genus *Pantoea*.

2. The bacterium according to claim 1, wherein the protein P is a protein selected from the group consisting of a PAJ_1175 protein, a PAJ_1174 protein, a PAJ_1173 protein, and combinations thereof.

3. The bacterium according to claim 2, wherein at least the activity of the PAJ_1175 protein is increased, or at least the activities of the PAJ_1174 protein and PAJ_1173 protein are increased.

4. The bacterium according to claim 1, wherein the activity of the protein P is increased by increasing the expression of a gene encoding the protein P.

5. The bacterium according to claim 4, wherein the expression of the gene encoding the protein P is increased by a method selected from the group consisting of:
(1) increasing the copy number of the gene encoding the protein P;
(2) modifying an expression control sequence of the gene encoding the protein P;
(3) reducing the activity of the c1795 protein; and
(4) combinations thereof.

6. The bacterium according to claim 1, wherein the activity of the c1795 protein is reduced by reducing the expression of a c1795 gene and/or disrupting a c1795 gene.

7. The bacterium according to claim 6, wherein the expression of the c1795 gene is reduced by modifying an expression control sequence of the c1795 gene.

8. The bacterium according to claim 1, wherein the activity of the c1795 protein is reduced by deleting a part of or the entirety of the amino acid sequence of the c1795 protein.

9. The bacterium according to claim 8, wherein the activity of the c1795 protein is reduced by a method selected from the group consisting of:
A) deletion of a partial or the entire region of the coding region of the c1795 gene,
B) introduction of a stop codon into the coding region of the c1795 gene,
C) introduction of a frame shift into the coding region of the c1795 gene, and
D) combinations thereof.

10. The bacterium according to claim 1, wherein the c1795 protein is selected from the group consisting of:
(a) a protein comprising the amino acid sequence of SEQ ID NO: 2;

(b) a protein comprising the amino acid sequence of SEQ ID NO: 2, but which includes substitution, deletion, insertion, and/or addition of 1 to 10 amino acid residues, and having a function of a c1795 protein; and (c) a protein comprising an amino acid sequence having an identity of 90% or higher to the amino acid sequence of SEQ ID NO: 2, and having a function of a c1795 protein;

wherein the function of a c1795 protein is as a transcriptional regulator of the Rrf2 family.

11. The bacterium according to claim 2, wherein the PAJ_1175 protein is selected from the group consisting of:
(a) a protein comprising the amino acid sequence of SEQ ID NO: 4;
(b) a protein comprising the amino acid sequence of SEQ ID NO: 4, but which includes substitution, deletion, insertion, and/or addition of 1 to 10 amino acid residues, and having a function of a PAJ_1175 protein; and
(c) a protein comprising an amino acid sequence having an identity of 90% or higher to the amino acid sequence of SEQ ID NO: 4, and having a function of a PAJ_1175 protein;
wherein the function of a PAJ_1175 protein is as a transcriptional regulatory of the AraC family.

12. The bacterium according to claim 2, wherein the PAJ_1174 protein is selected from the group consisting of:
(a) a protein comprising the amino acid sequence of SEQ ID NO: 6;
(b) a protein comprising the amino acid sequence of SEQ ID NO: 6, but which includes substitution, deletion, insertion, and/or addition of 1 to 10 amino acid residues, and having a function of a PAJ_1174 protein; and
(c) a protein comprising an amino acid sequence having an identity of 90% or higher to the amino acid sequence of SEQ ID NO: 6, and having a function of a PAJ_1174 protein;
wherein the function of a PAJ_1174 protein is as a periplasm adapter subunit of a multi-drug efflux transporter belonging to the RND (resistance-nodulation-cell division) superfamily.

13. The bacterium according to claim 2, wherein the PAJ_1173 protein is selected from the group consisting of:
(a) a protein comprising the amino acid sequence of SEQ ID NO: 8;
(b) a protein comprising the amino acid sequence of SEQ ID NO: 8, but which includes substitution, deletion, insertion, and/or addition of 1 to 10 amino acid residues, and having a function of a PAJ_1173 protein; and
(c) a protein comprising an amino acid sequence having an identity of 90% or higher to the amino acid sequence of SEQ ID NO: 8, and having a function of a PAJ_1173 protein;
wherein the function of a PAJ_1173 protein is as a permease subunit of a multi-drug efflux transporter belonging to the RND (resistance-nodulation-cell division) superfamily.

14. The bacterium according to claim 1, wherein the bacterium is a *Pantoea* bacterium or an *Escherichia* bacterium.

15. The bacterium according to claim 14, wherein the bacterium is *Pantoea ananatis* or *Escherichia coli*.

16. A method for producing an L-amino acid, the method comprising:
culturing the bacterium according to claim 1 in a medium to accumulate the L-amino acid in the medium and/or cells of the bacterium; and
collecting the L-amino acid from the medium and/or the cells.

17. The method according to claim 16, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

18. The method according to claim 16, wherein the L-amino acid is selected from the group consisting of L-glutamic acid, L-lysine, L-threonine, L-tryptophan, and combinations thereof.

19. The method according to claim 16, wherein the L-amino acid is L-glutamic acid.

20. The method according to claim 17, wherein the L-glutamic acid is monoammonium L-glutamate or monosodium L-glutamate.

21. A bacterium belonging to the family Enterobacteriaceae and having an L-amino acid-producing ability,
wherein the bacterium has a feature selected from the group consisting of:
(A) the bacterium has been modified so that the activity of a c1795 protein is reduced; and
(B) the bacterium has been modified so that the activity of a protein P is increased, wherein the expression of protein P is repressed by a c1795 protein,
wherein the protein P is a protein selected from the group consisting of a PAJ_1175 protein, a PAJ_1174 protein, a PAJ_1173 protein, and combinations thereof,
wherein the c1795 protein is selected from the group consisting of:
(a) a protein comprising the amino acid sequence of SEQ ID NO: 2;
(b) a protein comprising the amino acid sequence of SEQ ID NO: 2, but which includes substitution, deletion, insertion, and/or addition of 1 to 10 amino acid residues, and having a function of a c1795 protein; and
(c) a protein comprising an amino acid sequence having an identity of 90% or higher to the amino acid sequence of SEQ ID NO: 2, and having a function of a c1795 protein;
wherein the function of a c1795 protein is as a transcriptional regulator of the Rrf2 family,
wherein the PAJ_1175 protein is selected from the group consisting of:
(a) a protein comprising the amino acid sequence of SEQ ID NO: 4;
(b) a protein comprising the amino acid sequence of SEQ ID NO: 4, but which includes substitution, deletion, insertion, and/or addition of 1 to 10 amino acid residues, and having a function of a PAJ_1175 protein; and
(c) a protein comprising an amino acid sequence having an identity of 90% or higher to the amino acid sequence of SEQ ID NO: 4, and having a function of a PAJ_1175 protein;
wherein the function of a PAJ_1175 protein is as a transcriptional regulator of the AraC family,
wherein the PAJ_1174 protein is selected from the group consisting of:
(a) a protein comprising the amino acid sequence of SEQ ID NO: 6;
(b) a protein comprising the amino acid sequence of SEQ ID NO: 6, but which includes substitution, deletion, insertion, and/or addition of 1 to 10 amino acid residues, and having a function of a PAJ_1174 protein; and (c) a protein comprising an amino acid sequence having an identity of 90% or higher to the amino acid sequence of SEQ ID NO: 6, and having a function of a PAJ_1174 protein;

wherein the function of a PAJ_1174 protein is as a periplasm adapter subunit of a multi-drug efflux transporter belonging to the RND (resistance-nodulation-cell division) superfamily, wherein the PAJ_1173 protein is selected from the group consisting of:

(a) a protein comprising the amino acid sequence of SEQ ID NO: 8;

(b) a protein comprising the amino acid sequence of SEQ ID NO: 8, but which includes substitution, deletion, insertion, and/or addition of 1 to 10 amino acid residues, and having a function of a PAJ_1173 protein; and (c) a protein comprising an amino acid sequence having an identity of 90% or higher to the amino acid sequence of SEQ ID NO: 8, and having a function of a PAJ_1173 protein;

wherein the function of a PAJ_1173 protein is as a permease subunit of a multi-drug efflux transporter belonging to the RND (resistance-nodulation-cell division) superfamily.

22. A method for producing an L-amino acid, the method comprising:

culturing the bacterium according to claim 21 in a medium to accumulate the L-amino acid in the medium and/or cells of the bacterium; and collecting the L-amino acid from the medium and/or the cells.

* * * * *